(12) United States Patent
Lu et al.

(10) Patent No.: US 8,512,421 B2
(45) Date of Patent: Aug. 20, 2013

(54) POLYURETHANE DERIVATIVES, COMPOSITION THEREOF AND DYE ADDITIVES COMPRISING THE POLYURETHANE DERIVATIVES

(71) Applicant: Everlight Chemical Industrial Corporation, Taipei (TW)

(72) Inventors: Hsin-Ying Lu, Taoyuan (TW);
Sheue-Rong Lee, Taoyuan (TW);
Tzu-Heng Ko, Taoyuan (TW);
Hsiang-Lin Chiang, Taoyuan (TW);
Der-Gun Chou, Taoyuan (TW)

(73) Assignee: Everlight Chemical Industrial Corporation, Taipei (TW)

( * ) Notice: Subject to any disclaimer, the term of this patent is extended or adjusted under 35 U.S.C. 154(b) by 0 days.

(21) Appl. No.: 13/622,262

(22) Filed: Sep. 18, 2012

(65) Prior Publication Data

US 2013/0067664 A1    Mar. 21, 2013

(30) Foreign Application Priority Data

Sep. 19, 2011 (TW) ............................. 100133580 A

(51) Int. Cl.
*C09B 67/42* (2006.01)
*C07D 403/02* (2006.01)

(52) U.S. Cl.
USPC .................... 8/565; 8/566; 544/112; 544/113

(58) Field of Classification Search
USPC ............................... 8/565, 566; 544/112, 113
See application file for complete search history.

(56) References Cited

U.S. PATENT DOCUMENTS

| | | | |
|---|---|---|---|
| 4,812,139 A | 3/1989 | Brodmann | |
| 5,142,059 A | 8/1992 | Burdeska et al. | |
| 5,459,222 A * | 10/1995 | Rodgers et al. | 528/73 |
| 6,391,065 B1 | 5/2002 | Cooke | |

FOREIGN PATENT DOCUMENTS

| | | |
|---|---|---|
| CA | 1 197 246 | 11/1985 |
| JP | 2001-019681 | 1/2001 |
| TW | 200536837 | 11/2005 |

OTHER PUBLICATIONS

STIC Search Report dated Apr. 5, 2013.*

* cited by examiner

*Primary Examiner* — Eisa Elhilo
(74) *Attorney, Agent, or Firm* — Muncy, Geissler, Olds & Lowe, PLLC

(57) ABSTRACT

A polyurethane derivative and a composition thereof are disclosed. The polyurethane derivative of the present invention has a structure of formula (I). The polyurethane derivative and the composition thereof can be used for increasing light fastness.

-continued
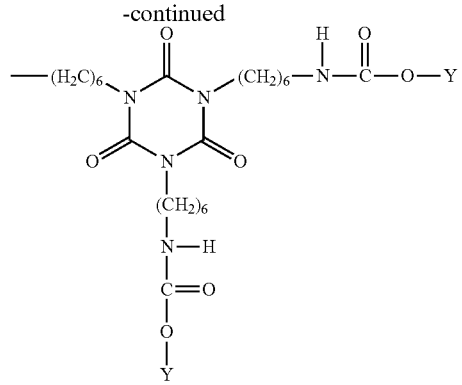
13 Claims, 13 Drawing Sheets

POLYURETHANE DERIVATIVES, COMPOSITION THEREOF AND DYE ADDITIVES COMPRISING THE POLYURETHANE DERIVATIVES

1. FIELD OF INVENTION

The present invention relates to polyurethane derivatives and compositions having the polyurethane derivative, and more particularly, to a polyurethane derivative and a composition having the polyurethane derivative for increasing light fastness.

2. BACKGROUND OF THE INVENTION

A process of dyeing includes a pre-treatment (such as singeing, desizing, scouring, bleaching, mercerizing, heat setting), printing and dyeing, and post-dyeing (such as finishing). In the pre-treatment, impurity, a paste and an auxiliary agent on a textile are removed to facilitate the subsequent procedure. In the post-dyeing procedure, the property (such as color fastness, appearance, anti-shrinkage, anti-static electricity, flame-proof, water-proof, oil repellence and the like) of the textile is enhanced.

In order to prevent photo-degradation due to exposure to sun light (UV), a light fastness increasing agent (for example, a UV light absorbing agent or a light stabilizing agent) is added in the post-dyeing procedure to maintain the lifespan of the textile. There are various materials used for increasing light fastness of a textile. Publication No. TW200804196 discloses that the solution of ZnO and $TiO_2$ is capable of absorbing UV and can be used for treating a textile so as to increase light fastness of the textile. Patent No. CA1,197,246 discloses that 2-(2'-hydroxyphenyl)-benzotriazole have great ability to absorb UV light. However, these compounds have poor affinity to water, and thus only can used for specific textiles and dyes. Further, benzotriazole have poor fastness and poor tolerance to washing. In addition, these compounds are accompanied a significant amount of organic solvent, and need to be added a surfactant to form an additive. Publication No. JP2001-019681, U.S. Pat. No. 5,142,059 and Publication No. TW200536837 disclose benzotriazole with affinity to water; however, these compounds have poor fastness, low yield and a significant amount of organic solvent accompanied therewith. Similarly, these compounds need a surfactant to form a light fastness increasing agent.

U.S. Pat. Nos. 5,459,222, 6,391,065 and 4,812,139 disclose UV absorbing agents containing benzotriazole or benzophenone. These compounds have great ability to absorb UV light, but can be only used in polyester fibers. Further, these compounds are generally accompanied with a significant amount (for example, 60-95%) of organic solvents, and need surfactants for emulsification to form an additive (such as a light fastness increasing agent), which has adverse effects to environmental protections.

Hence, there is a need to develop a compound with a great dispersion for forming a light fastness increasing agent to be used in various textiles.

SUMMARY OF THE INVENTION

The present invention provides a novel compound and a composition having the novel compound for increasing light fastness.

In accordance with the present invention, the polyurethane derivative has a structure of formula (I):

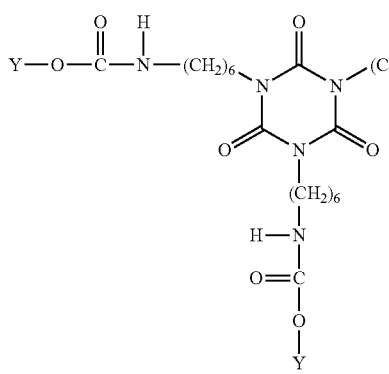

wherein A is one selected from the group consisting of

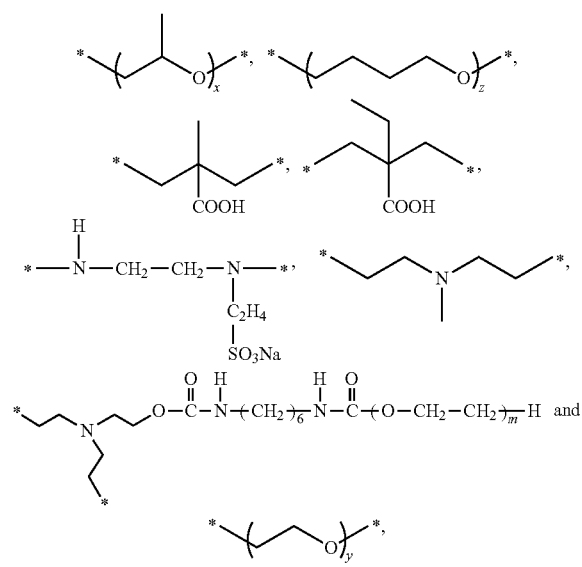

wherein x is an integer in a range of from 15 to 20, z is an integer in a range of from 10 to 15, m is an integer in a range of from 15 to 20, y is an integer in a range of from 20 to 50, and * indicates a position to be bound with M1 or M2, in which

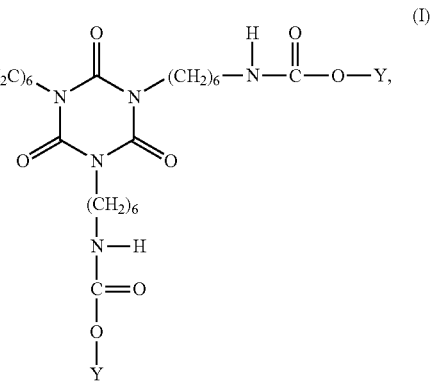

M1 and M2 are independently —NHCOO— or —NHCO—; and Y is one selected from the group consisting of

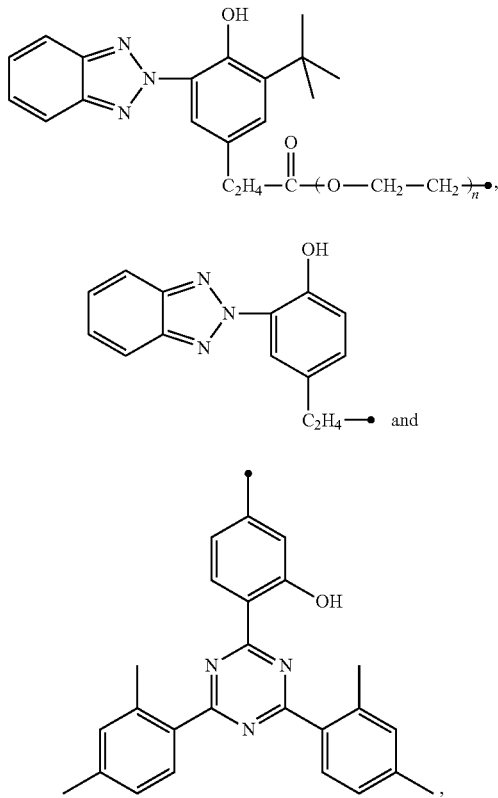

in which n is an integer in a range from 7 to 9, ● indicates a position to be bound with —O—, and each Y is identical or different.

The present invention further provides a composition for increasing light fastness. The composition of the present invention includes at least one polyurethane derivative having the structure of formula (I).

In accordance with the present invention, the polyurethane derivative and the composition having the polyurethane derivative have great ability to attach on a textile and increase light fastness of a coating material (such as a dye) on the textile.

In addition, the dye additive including the polyurethane derivative of formula (I) has extremely low amount of an organic solvent. Further, the polyurethane derivative of formula (I) and the composition thereof are water soluble, and need no surfactant to form the solution for treating a textile. Hence, the polyurethane derivative of formula (I), the composition and the dye additive having the polyurethane derivative meet the requirement of environment protection.

DETAILED DESCRIPTION OF THE PREFERRED EMBODIMENTS

Figure 1:
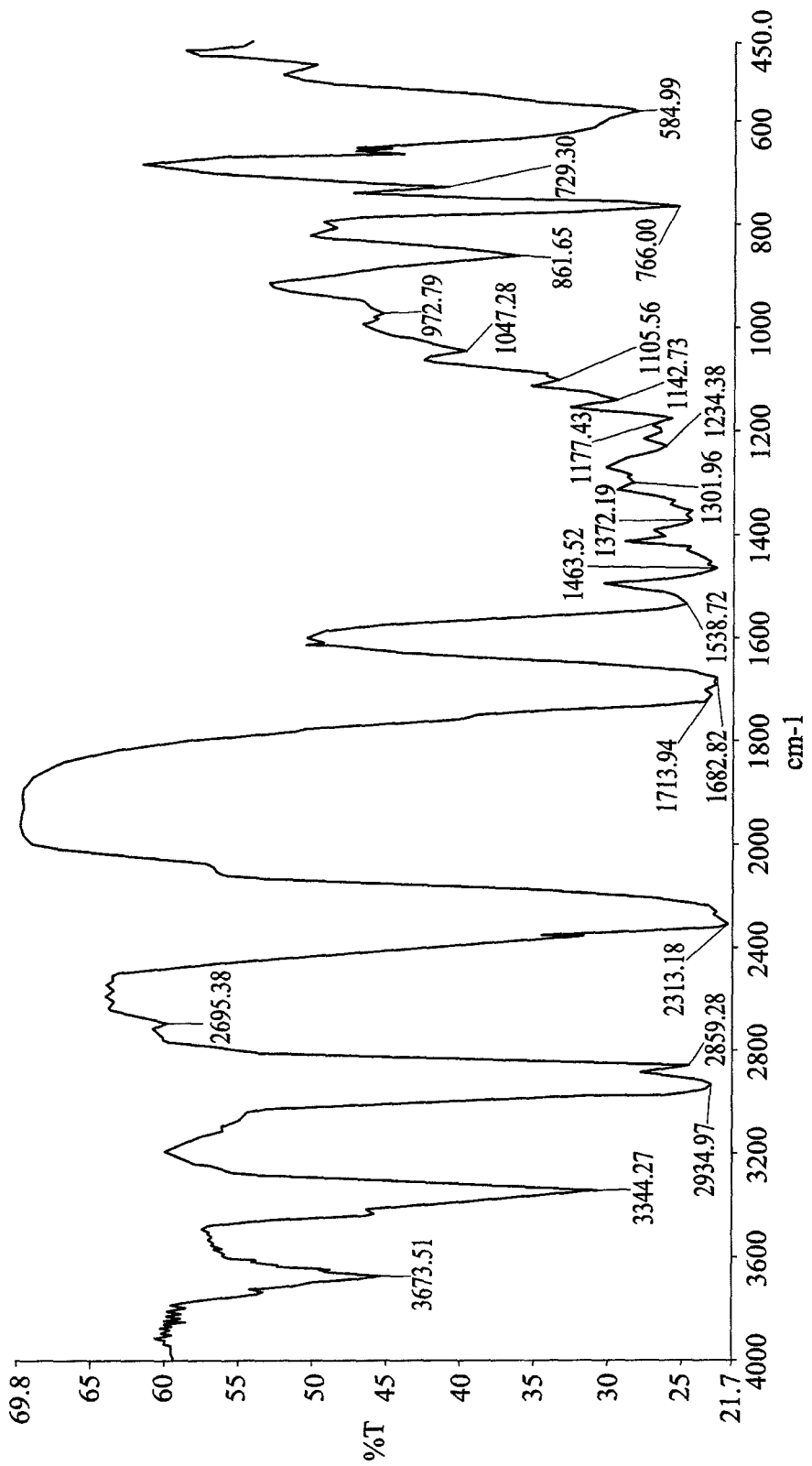
FIG. 1 is the IR spectrum of THDI.

The following specific examples are used for illustrating the present invention. A person skilled in the art can easily conceive the other advantages and effects of the present invention.

The term "weight average molecular weight" herein is an Mw value of polystyrene measured by using gel permeation chromatography (GPC) solvent: tetrahydrofuran (THF).

The present invention provides a polyurethane derivative having a structure of formula (I):

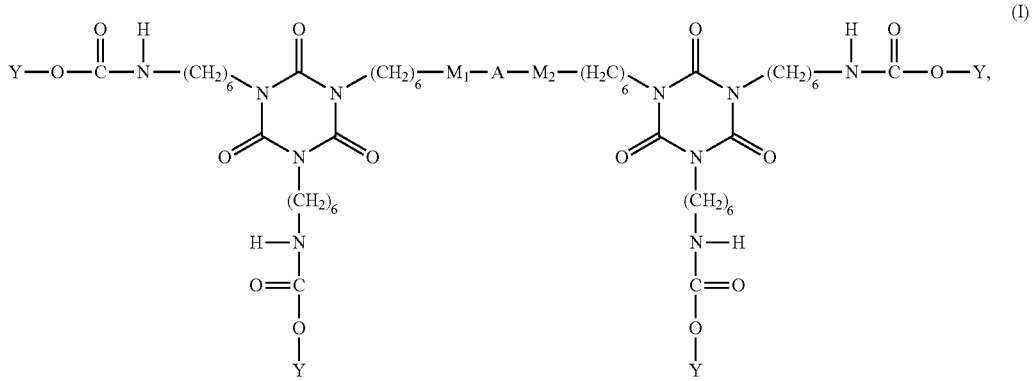

wherein A is one selected from the group consisting of

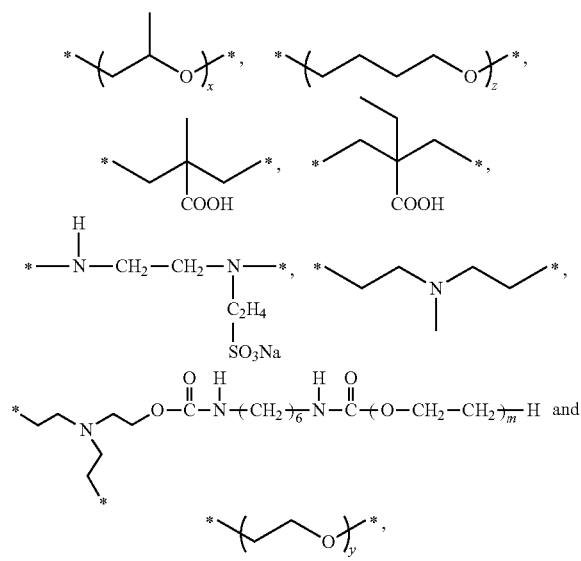

wherein x is an integer in a range of from 15 to 20, z is an integer in a range of from 10 to 15, m is an integer in a range of from 15 to 20, y is an integer in a range of from 20 to 50, and * indicates a position to be bound with M1 or M2, in which M1 and M2 are independently —NHCOO— or —NHCO—; and Y is one selected from the group consisting of

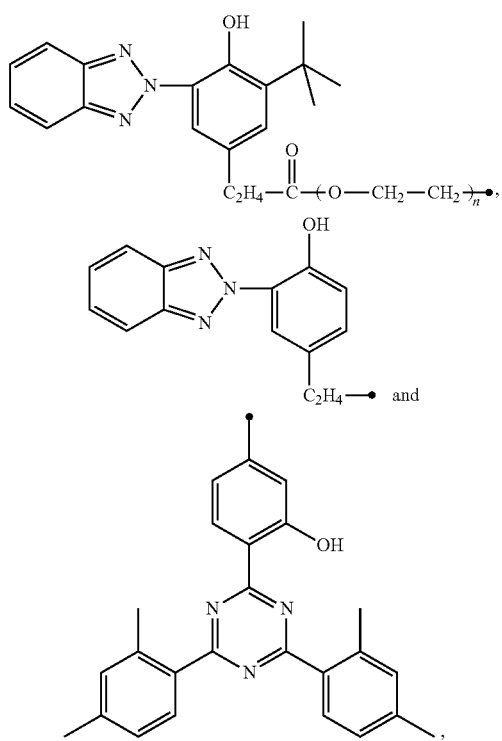

in which n is an integer in a range from 7 to 9, ● indicates a position to be bound with —O—, and each Y is identical or different.

In accordance with an embodiment of the present invention, in the polyurethane derivative having a structure of formula (I), A is

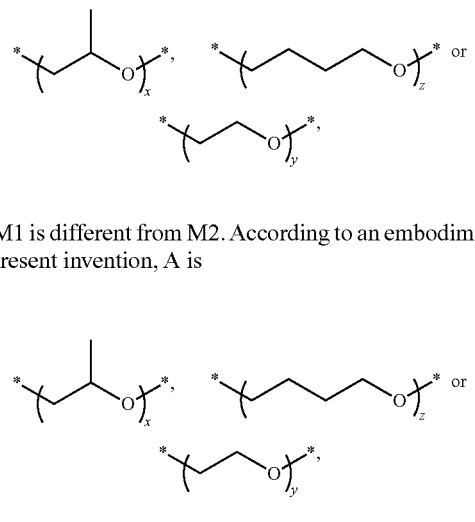

and M1 is different from M2. According to an embodiment of the present invention, A is

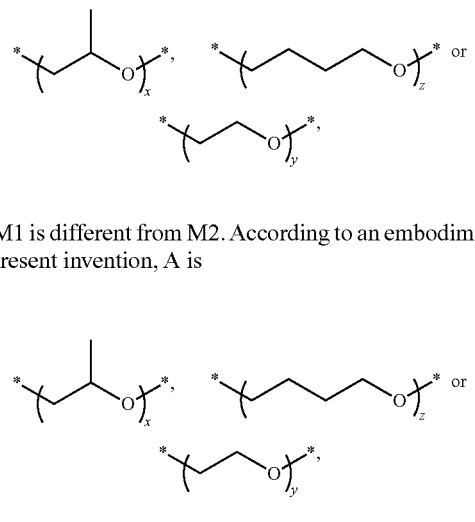

one of M1 and M2 is —NHCOO— and the other one is —NHCO—.

In accordance with an embodiment of the present invention, in the polyurethane derivative having a structure of formula (I), A is

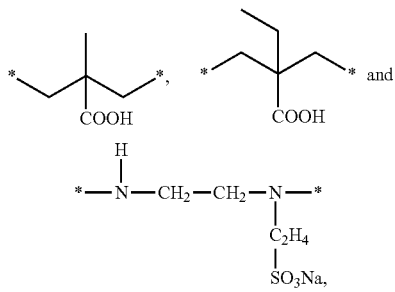

and M1 and M2 are the same. When A is one of

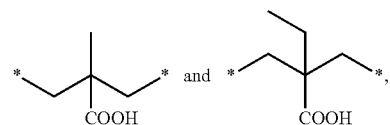

each of M1 and M2 is —NHCOO—. When A is

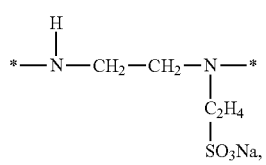

each of M1 and M2 is —NHCO—.

In accordance with an embodiment of the present invention, in the polyurethane derivative having a structure of formula (I), A is

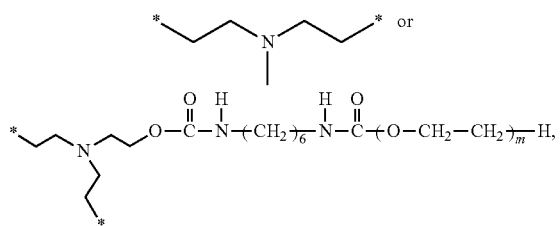 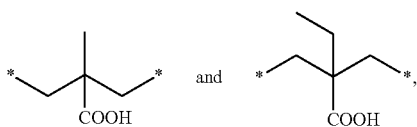

and each of M1 and M2 is —NHCOO—.

In accordance with an embodiment of the present invention, in the polyurethane derivative having a structure of formula (I), Y is

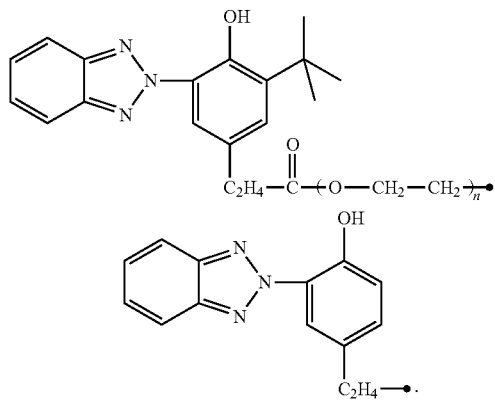

In this embodiment of the present invention, A is

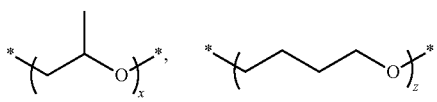

or

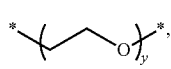

one of M1 and M2 is —NHCOO—, and the other one is —NHCO—. In another embodiment of the present invention, A is

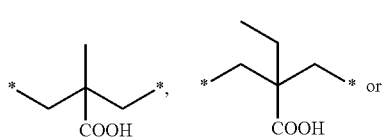

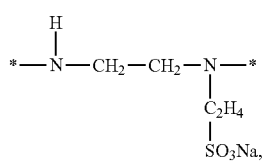

and M1 and M2 are the same. When A is one of

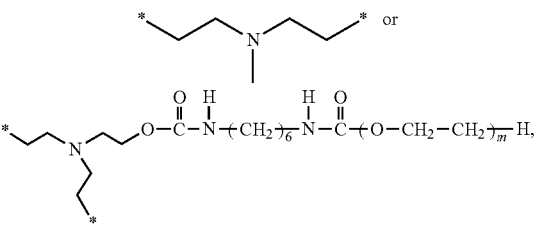

each of M1 and M2 is —NHCOO—. When A is

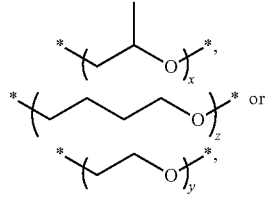

each of M1 and M2 is —NHCO—. In another embodiment of the present invention, A is

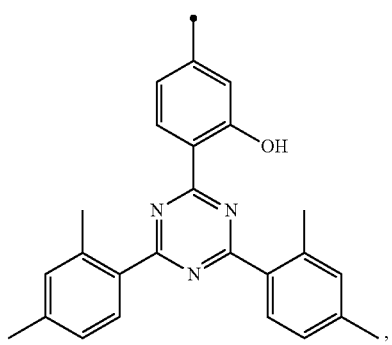

each of M1 and M2 is —NHCOO—.

In accordance with an embodiment of the present invention, in the polyurethane derivative having a structure of formula (I), Y is A is one of M1 and M2 is —NHCOO—, and the other one is —NHCO—. In this embodiment, Y is

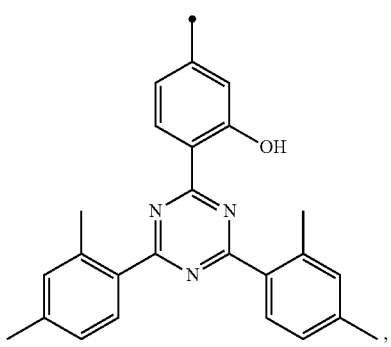

A is

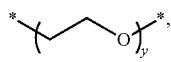

one of M1 and M2 is —NHCOO—, the other one is —NHCO—.

The polyurethane derivative having a structure of formula (I) can be prepared by the conventional method. For example, the polyurethane derivative having a structure of formula (I) can be prepared by the following method or similar methods. A reaction of a tris diisocyanate hexylmethyl ester (such as THDI, 1,3,5-tris(6-isocyanatohexyl)-1,3,5-triazinane-2,4,6-trione, or an analog thereof) and a material having Y residue is performed to form a tris diisocyanate hexylmethyl ester derivative with a chain-extending component having Y. This reaction may be performed by the conventional method (such as the method described by Seymour. Carraher in Polymer Chemistry). This reaction may be performed in a solvent, which has no adverse effects to the reaction.

The above solvent may be, but not limited to, DMAc (N,N-Dimethylacetamide), DMF (N,N-dimethylmethanamide), NMP (1-methyl-2-pyrrolidone), MEK (butanone), acetone, EAc (ethyl ethanoate), BAc (butyl acetate) or a combination thereof. There is no specific limitation to the amount of the solvent, which may alter with different solvent and reaction conditions.

The above reaction is performed at the temperature in a range from about 70 to 95° C.

The above reaction is performed for about 2 to 4 hours.

Subsequently, the reaction is added with a material having A residue, and then is performed to form a polyurethane derivative having a structure of formula (I). This reaction may be performed by the conventional method (such as the method described by Seymour. Carraher in Polymer Chemistry). This reaction may be performed in a solvent, which has no adverse effects to the reaction.

The above solvent may be, but not limited to, DMAc (N,N-Dimethylacetamide), DMF (N,N-dimethylmethanamide), NMP (1-methyl-2-pyrrolidone), MEK (butanone), acetone, EAc (ethyl ethanoate), BAc (butyl acetate) or a combination thereof. There is no specific limitation to the amount of the solvent, which may alter with different solvent and reaction conditions.

The above reaction is performed at the temperature in a range from about 70 to 95° C.

The above reaction is performed for about 2 to 4 hours.

The preparation method is described in detail as follows. The polyurethane derivative having a structure of formula (I) can be prepared by the following method or similar methods. The method for preparing the polyurethane derivative having a structure of formula (I) (for example, synthesis method, reaction conditions or sequence) is not limited to the description of the present invention. Various materials and preparation methods may be used for forming the polyurethane derivative having a structure of formula (I).

In the present invention, the polyurethane derivative having a structure of formula (I) has great water dispersion (water soluble), and can be added with water to form a solution for treating a material (such as a textile) or to be an additive for a dye without a surfactant. An additive (such as a surfactant) may be optionally added in the composition of the present invention.

While the polyurethane derivative having a structure of formula (I) has a carboxyl group or a sulfonyl group in the group A, the polyurethane derivative may be added with an alkali before forming an aqueous solution. The alkali may be, but not limited to, triethylamine, DMEA (N,N-dimethylethanolamine), TEA (2,2',2"-nitrilotriethanol) or a combination thereof.

While the polyurethane derivative having a structure of formula (I) has a tertiary amine, the polyurethane derivative may be added with an acid before forming an aqueous solution. The addition of the acid may be performed in the synthesis of the polyurethane derivative having the structure of formula (I). For example, the acid may be added to neutralize the material having the group A (having the tertiary amine). The acid may be, but not limited to, AcOH (acetic acid), MSA (methanesulfonic acid), PTSA (4-methylbenzenesulfonic acid) or a combination thereof.

The present invention provides a composition including the compound of formula (I) for increasing light fastness.

According to an embodiment of the present invention, the composition includes a polyurethane derivative of formula (I), wherein Y is

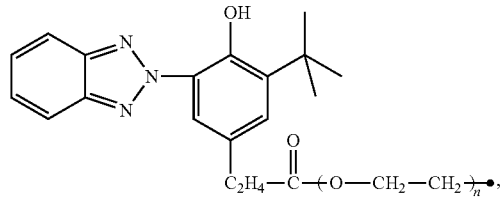

A is

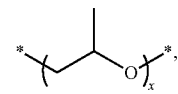

one of M1 and M2 is —NHCOO—, and the other one is —NHCO—; and another polyurethane derivative of formula (I), wherein Y is

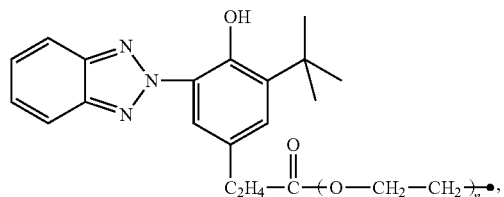

A is

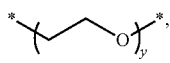

one of M1 and M2 is —NHCOO—, and the other one is —NHCO—.

In accordance with an embodiment of the present invention, the composition includes a polyurethane derivative of formula (I), wherein Y is

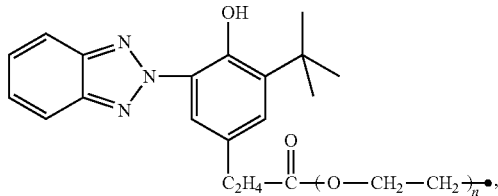

A is

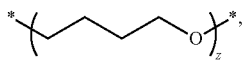

one of M1 and M2 is —NHCOO—, and the other one is —NHCO—; another polyurethane derivative of formula (I), wherein Y is

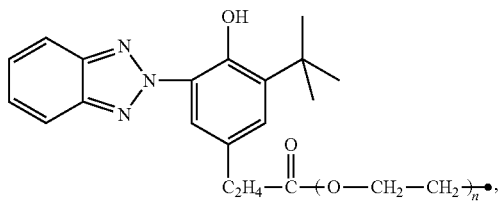

A is

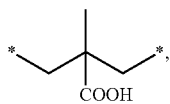

and each of M1 and M2 is —NHCOO—.

In the present invention, the polyurethane derivative having a structure of formula (I) has great water dispersion (water soluble), and can be added with water to form a solution for treating a material (such as a textile) or to be an additive for a dye without a surfactant. An additive (such as a surfactant) may be optionally added in the composition of the present invention.

In accordance with the present invention, the polyurethane derivative and the composition have great water dispersion, diffusion, storage stability and various applications. The polyurethane derivative of formula (I) may be used in various materials, which may be, but not limited to, a fiber, a leather (natural leather or artificial leather), a foam, a wood and the like. Particularly, the polyurethane derivative of formula (I) can be used in a fiber such as a natural fiber (for example, plant fibers, animal fibers (such as wool) and mineral fibers) and an artificial fiber (for example, regenerated fibers, semi synthetic fibers and synthetic fibers (such as polyester fibers or nylon fibers). Preferably, the fiber is a natural cellulose fiber (such as cotton, jute; flax, hemp, ramie and the like), an animal fiber (such as wools), a regenerated fiber (such as viscose rayon), and a synthetic fiber (such as polyester fibers or nylon fibers). More preferably, the fiber is cotton. The polyurethane derivative of formula (I) and the composition of the present invention can be used in a mixed fiber or a mixed textile containing the above fibers.

In accordance with the present invention, the composition may optionally include an auxiliary agent, which may be, but not limited to, a UV absorbing agent, a light stabilizing agent, an antioxidant, a surfactant, a leveling agent, a thickening agent, a defoaming agent or a combination thereof.

The polyurethane derivative and the composition of the present invention may be used with or without a coating material (such as a dye) for a substrate (such as wood, paper, leather, textiles, foam, fibers and the like). The polyurethane derivative of formula (I) and/or the composition of the present invention can be used in any stage of a dyeing process (for example, post-dyeing treatment). The polyurethane derivative of formula (I) and/or the composition of the present invention can be used for print dyeing a substrate in various ways (for example, dip dyeing, continuous dyeing, cold press dyeing, print dyeing, digital dyeing and the like). The polyurethane derivative of formula (I) and/or the composition of the present invention can be used with a dye such that the dyed substrate would have great light fastness and washing fastness.

The polyurethane derivative of formula (I) and the composition of the present invention may be used as an auxiliary agent with a dye. The dye may be, but not limited to, a disperse dye, a reactive dye, an acidic dye, a direct dye, a basic/cationic dye, a vat dye, a sulfur dye, a pigment and the like.

The present invention further provides a light fastness increasing agent, which includes at least a polyurethane derivative of formula (I).

The present invention provides a dye additive including at least a polyurethane derivative of formula (I).

The polyurethane derivative, the composition and the light fastness increasing agent and the dye additive of the present invention may be optionally used with other additives, which may be, but not limited to, a UV absorbing agent, a light stabilizing agent or an antioxidant.

The polyurethane derivative of formula (I) and the composition of the present invention have great attachment to a substrate (such as a textile), provide an anti-UV characteristic for the substrate, and increase light fastness and washing fastness of a coating material (for example, a dye) for a textile.

The light fastness increasing agent and the dye additive prepared from the polyurethane derivative of formula (I) and/or the composition of the present invention has an extremely low amount of an organic solvent. Moreover, the polyurethane derivative of formula (I) and/or the composition of the present invention are water soluble and thus need no surfactants for treating a substrate in an aqueous solution. Therefore, the polyurethane derivative of formula (I), the composition and the additive (for example, a light fastness increasing agent) meet requirements of the environmental protection.

The present invention is specifically described, but not limited by, the following embodiments. In the following embodiments and comparative examples, the content of any component is indicated as "%" or "weight part" on the basis of weight.

Embodiments
Preparations of compounds 1-10 and compositions 1-2
Preparation of Compounds 1-10
Embodiment 1: Compound 1

52.21 g of EV80 (α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl) (Everlight Chemical Industrial Corporation) was provided in a 125 ml flask, stirred, heated to 50° C., and added with 20.18 g of THDI (1,3,5-tris(6-isocyanatohexyl)-1,3,5-triazinane-2,4,6-trione) and 18.10 g of DMAc (N,N-dimethylacetamide). The mixture was heated to 90° C., and the reaction was performed for 2-3 hours (the NCO group was titrated till the end point of the reaction).

Figure 2:
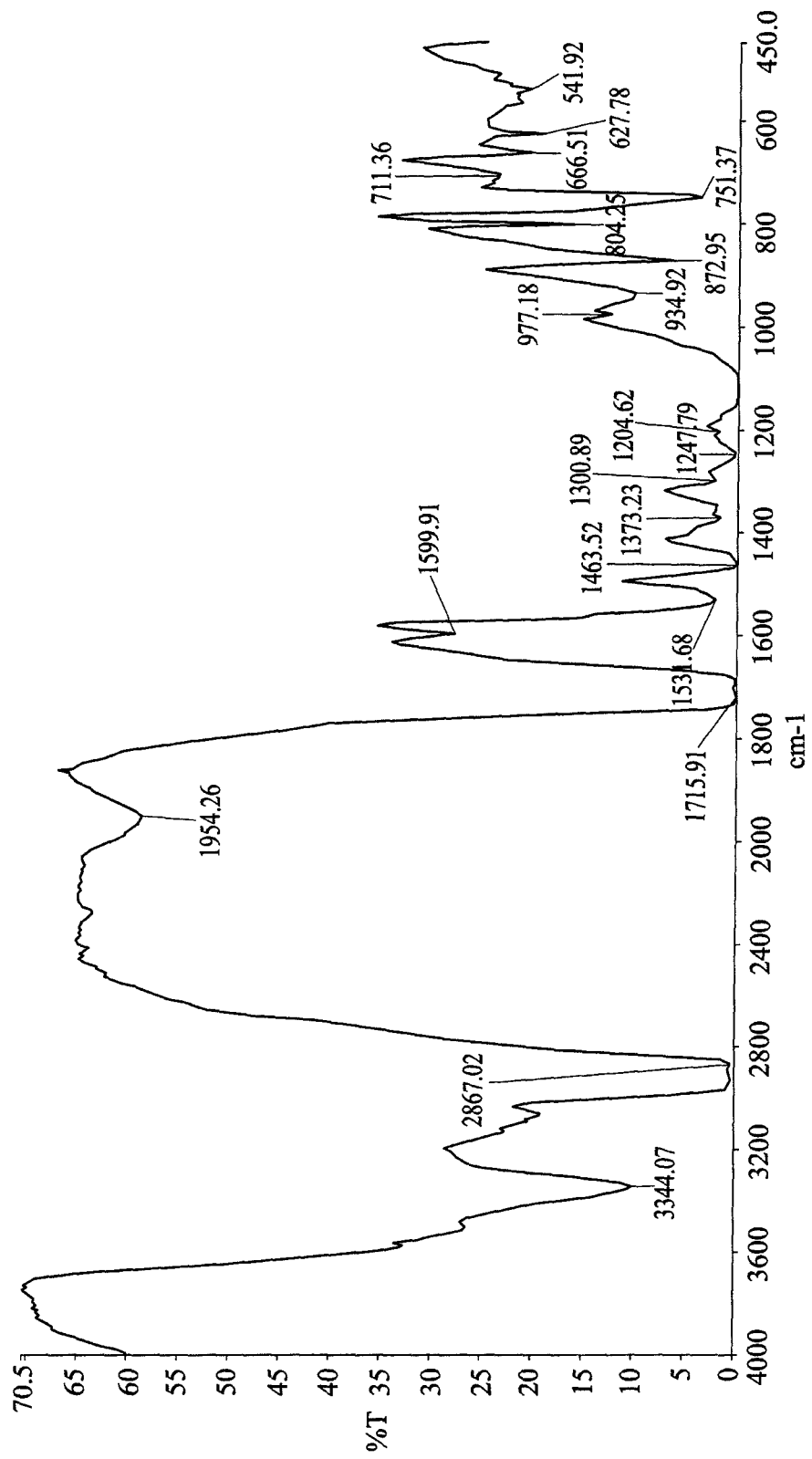
FIG. 2 is the IR spectrum according to the first embodiment of the present invention.

Then, the mixture was cooled down to 70° C., and then added with 12.40 g of DMAc and 19.45 g of PPG1000 (polypropylene glycol, Mw=1000). The mixture was heated to 90° C., and the reaction was performed for 2-3 hours (the NCO group was titrated till the end point of the reaction). Then, the mixture was cooled down to 50° C., and then the compound 1 having the following structure was obtained (Mw=4489.2, IR spectrum shown in FIG. 2, —NH peak sharp 3344.07 cm-1, C=O 1715.91 cm-1). As shown in FIG. 2, the two peaks indicated the NHCOO group, which was the specific group of PU and resulted from the reaction of —NCO and —OH. Referring to FIG. 1 and FIG. 2, there was a significant —NCO peak at 2313.18 cm-1 in THDI plot, but there is no —NCO peak in FIG. 2 indicating that the reaction of —NCO and —OH was performed completely.

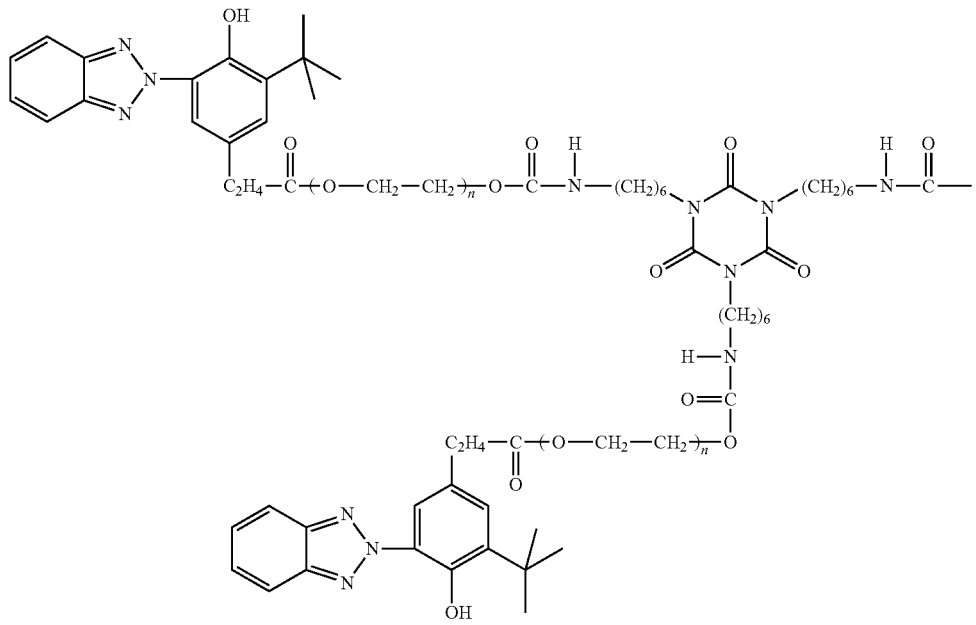

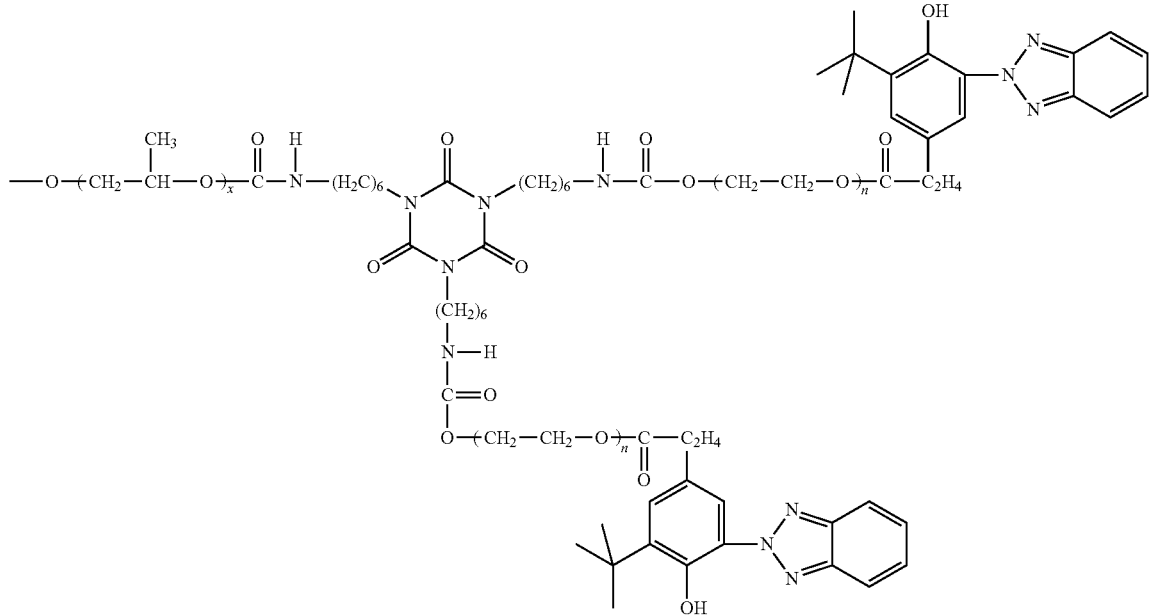

Embodiment 2: Compound 2

Figure 3:
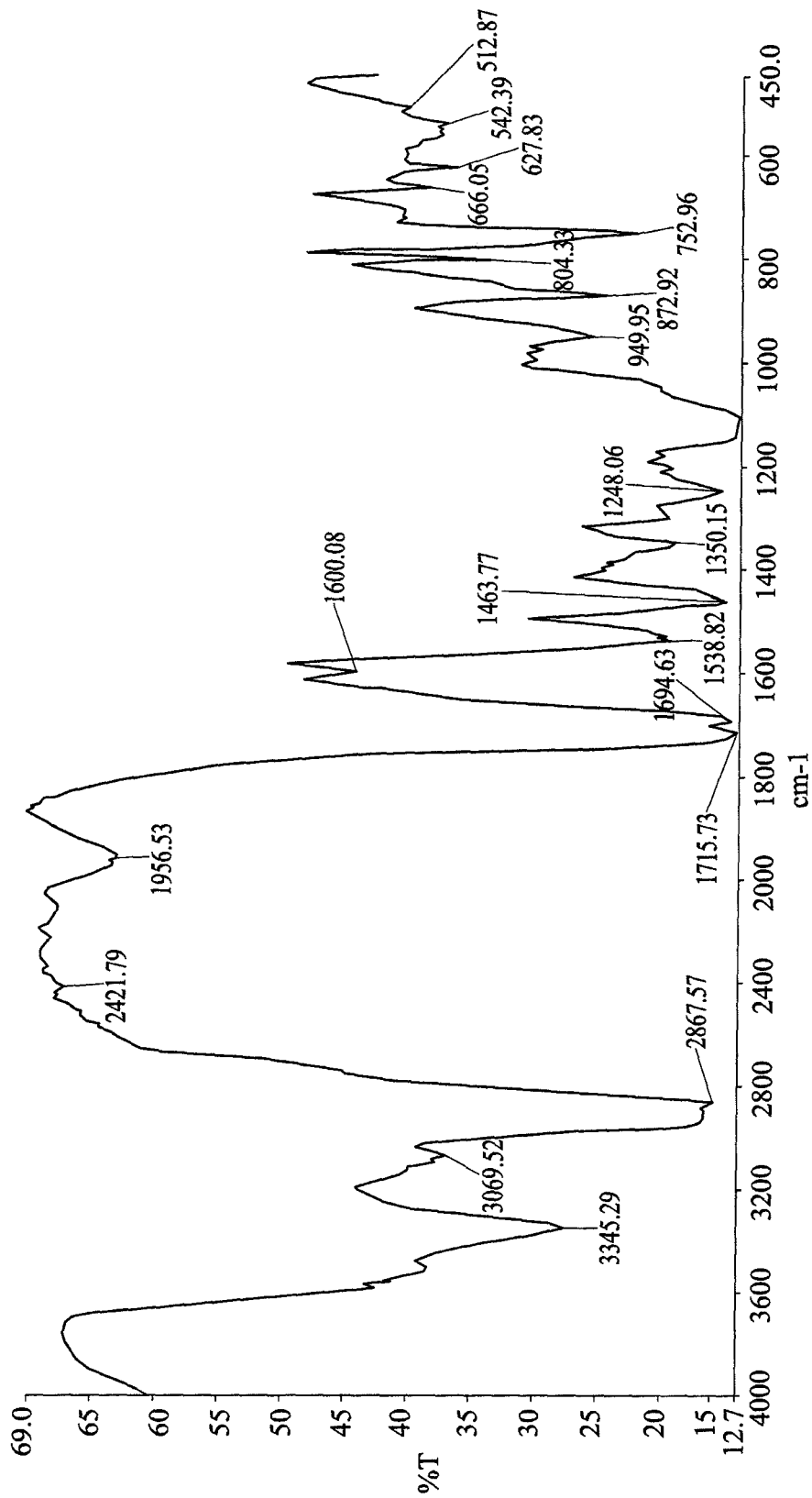
FIG. 3 is the IR spectrum according to the second embodiment of the present invention.

46.82 g of EV80 was provided in a 250 ml flask, stirred, heated to 50° C., and added with 18.67 g of THDI and 16.40 g of DMAc. The mixture was heated to 90° C., and the reaction was performed for 2-3 hours (the NCO group was titrated till the end point of the reaction). Then, the mixture was cooled down to 70° C., and then added with 11.30 g of DMAc and 18.00 g of PEG 1000 (polyethylene glycol, Mw=1000). The mixture was heated to 90° C., and the reaction was performed for 2-3 hours (the NCO group was titrated till the end point of the reaction). Then, the mixture was cooled down to 50° C., and then the compound 2 having the following structure was obtained (Mw=4489.2, IR spectrum shown in FIG. 3, —NH peak sharp 3345.29 cm-1, C=O peak sharp 1694.63~1715.73 cm-1). As shown in FIG. 3, the two peaks indicated the NHCOO group, which was the specific group of PU and resulted from the reaction of —NCO and —OH. Referring to FIG. 1 and FIG. 3, there was a significant —NCO peak at 2313.18 cm-1 in THDI plot, but there is no —NCO peak in FIG. 3 indicating that the reaction of —NCO and —OH was performed completely.

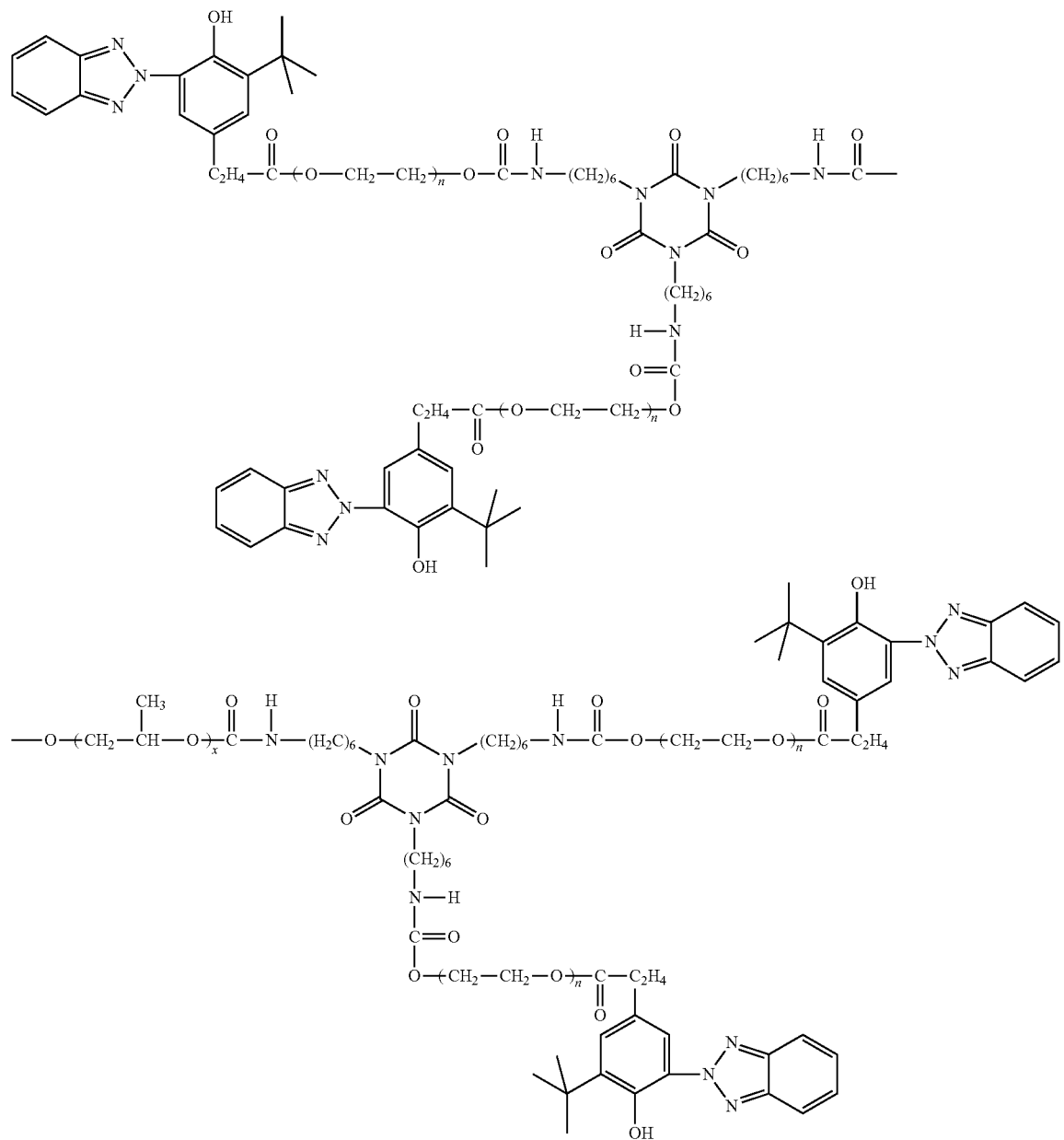

The compound 2 can be used with 163 g of pure water and stirred till dispersed completely.

Embodiment 3: Compound 3

Figure 4:
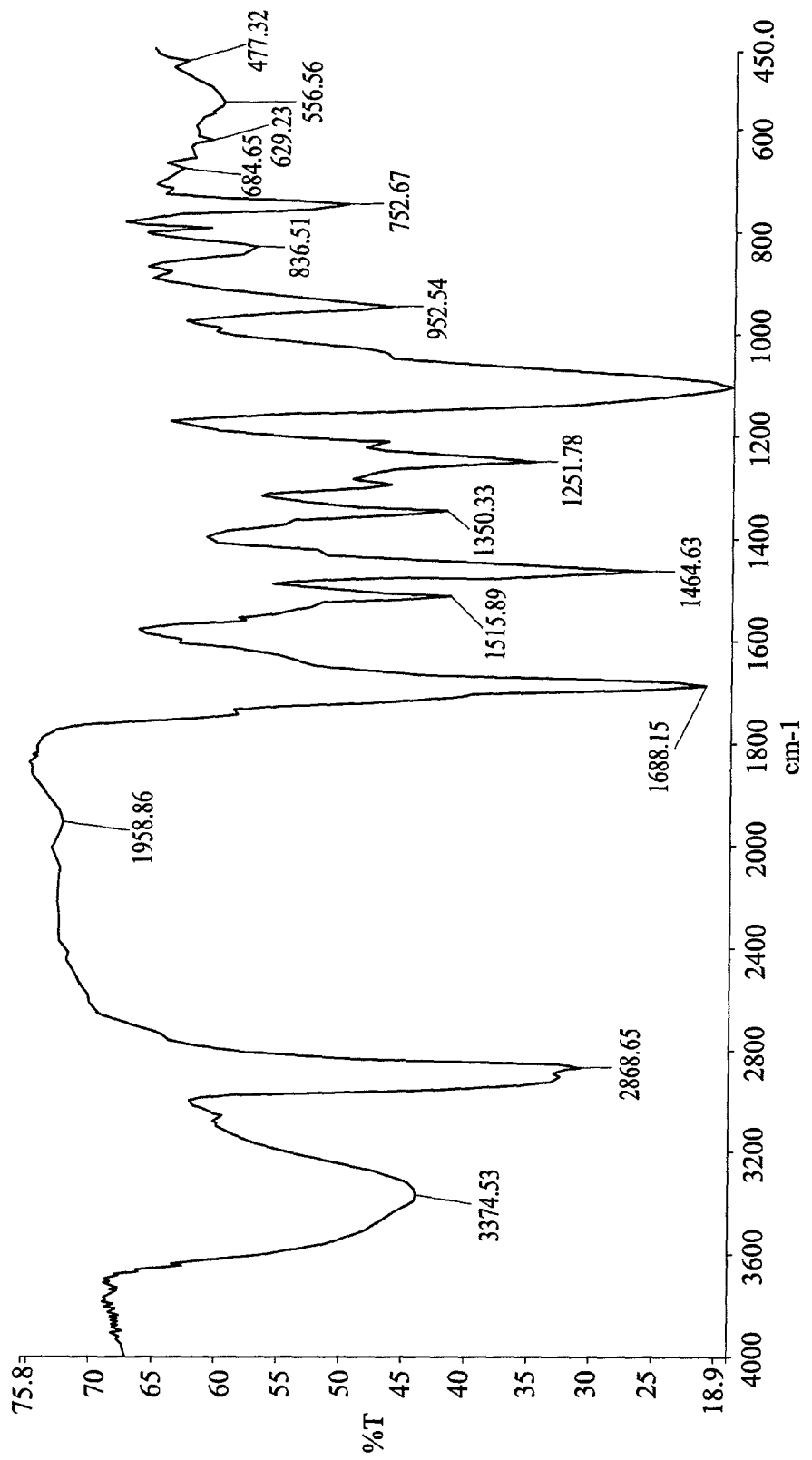
FIG. 4 is the IR spectrum according to the third embodiment of the present invention.

20.18 g of THDI and 27.30 g of DMAc were provided in a 250 ml flask, stirred, heated to 50° C., and then added with 20.82 g of R02 (2-(2H-benzo[d][1,2,3]triazol-2-yl)-4-(2-hydroxyethyl)phenol) (Everlight Chemical Industrial Corporation). Then, the mixture was heated to 90° C., and the reaction was performed for 2-3 hours (the NCO group was titrated till the end point of the reaction). Then, the mixture was cooled down to 70° C., and then added with 26.80 g of DMAc and 40.00 g of PEG2000 (Mw=2000). The mixture was heated to 90° C., and the reaction was performed for 2-3 hours (the NCO group was titrated till the end point of the reaction). The mixture was cooled down to 50° C., and then the compound 3 was obtained (Mw=4029.2, IR spectrum shown in FIG. 4, —NH peak sharp 3374.53 cm-1, C═O peak sharp 1688.15 cm-1). As shown in FIG. 4, the two peaks indicated the NHCOO group, which was the specific group of PU and resulted from the reaction of —NCO and —OH. Referring to FIG. 1 and FIG. 4, there was a significant —NCO peak at 2313.18 cm-1 in THDI plot, but there is no —NCO peak in FIG. 3 indicating that the reaction of —NCO and —OH was performed completely.

The compound 3 can be used with 135 g of pure water and stirred till dispersed completely.

Embodiment 4: Compound 4

18.17 g of THDI and 38.30 g of DMAc were provided in a 250 ml flask, stirred, heated to 50° C., and then added with 29.17 g of BTOD (4-(4,6-bis(2,4-dimethylphenyl)-1,3,5-triazin-2-yl)benzene-1,3-diol) (Everlight Chemical Industrial Corporation). Then, the mixture was heated to 90° C., and the reaction was performed for 2-3 hours (the NCO group was titrated till the end point of the reaction). Then, the mixture was cooled down to 70° C., and then added with 35.24 g of PEG2000 (Mw=2000). The mixture was heated to 90° C., and the reaction was performed for 2-3 hours (the NCO group was

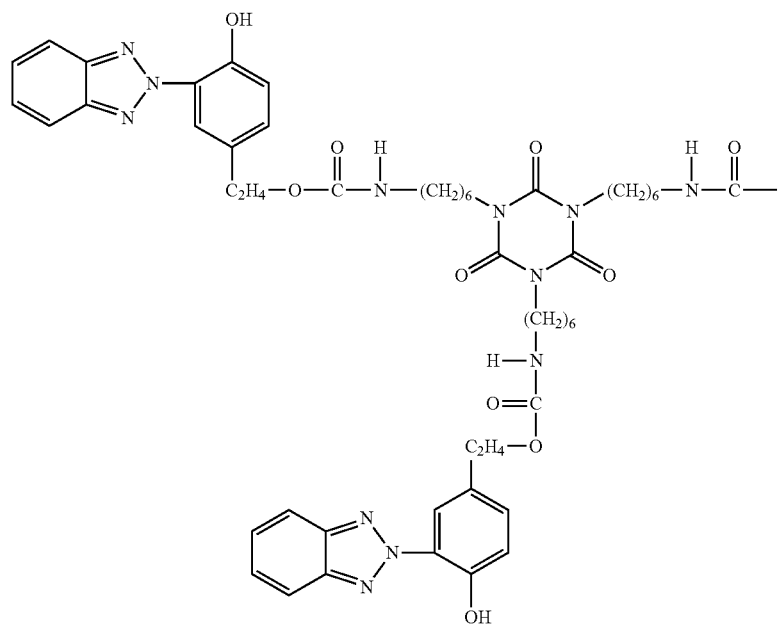

Figure 5:
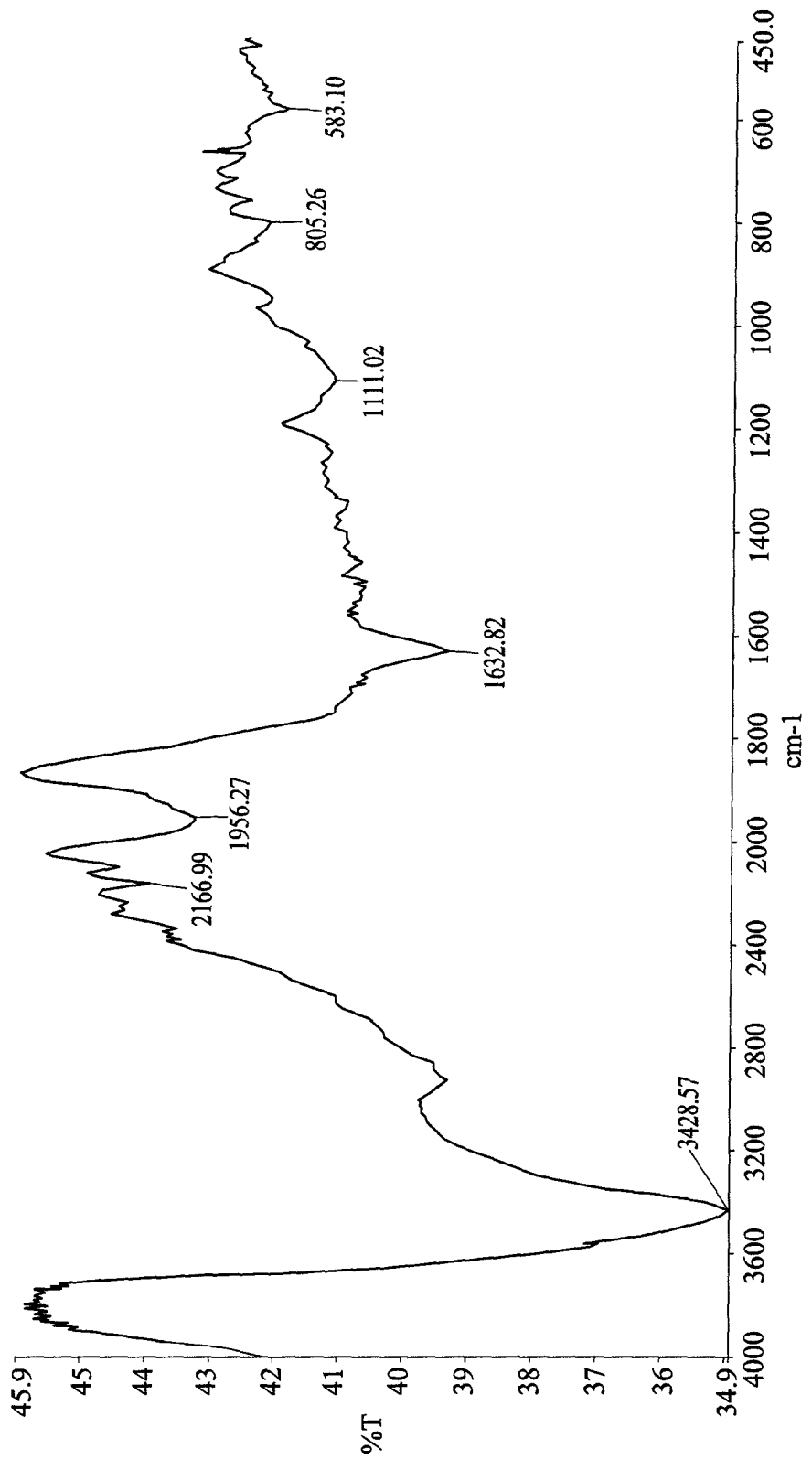
FIG. 5 is the IR spectrum according to the fourth embodiment of the present invention.

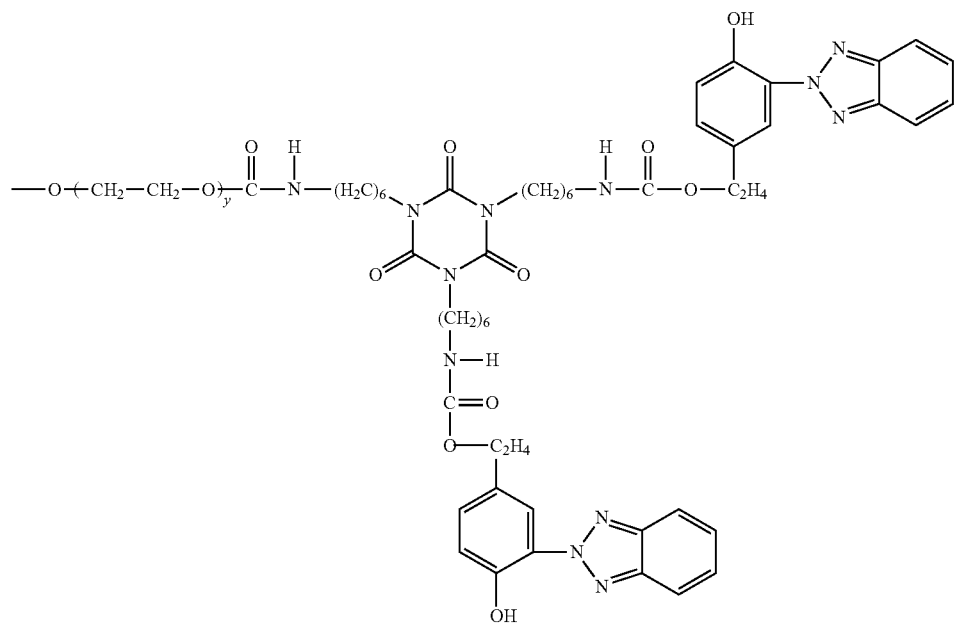

titrated till the end point of the reaction). The mixture was cooled down to 50° C., and then the compound 4 was obtained (Mw=4597.2, IR spectrum shown in FIG. 5, —NH peak sharp 3428.57 cm-1, C═O peak sharp 1632.82 cm-1). As shown in FIG. 5, the two peaks indicated the NHCOO group, which was the specific group of PU and resulted from the reaction of —NCO and —OH. Referring to FIG. 1 and FIG. 5, there was a significant —NCO peak at 2313.18 cm-1 in THDI plot, but there is no —NCO peak in FIG. 5 indicating that the reaction of —NCO and —OH was performed completely.

The compound 4 can be used with 153 g of pure water and stirred till dispersed completely.

Embodiment 5: Compound 5

52.21 g of EV80 was provided in a 250 ml flask, stirred, heated to 50° C., and added with 20.18 g of THDI and 18.10 g of DMAc. The mixture was heated to 90° C., and the reaction was performed for 2-3 hours (the NCO group was titrated till the end point of the reaction). Then, the mixture was cooled down to 70° C., and then added with 12.40 g of DMAc and 19.45 g of PTMG1000 (polytetramethylene gly-

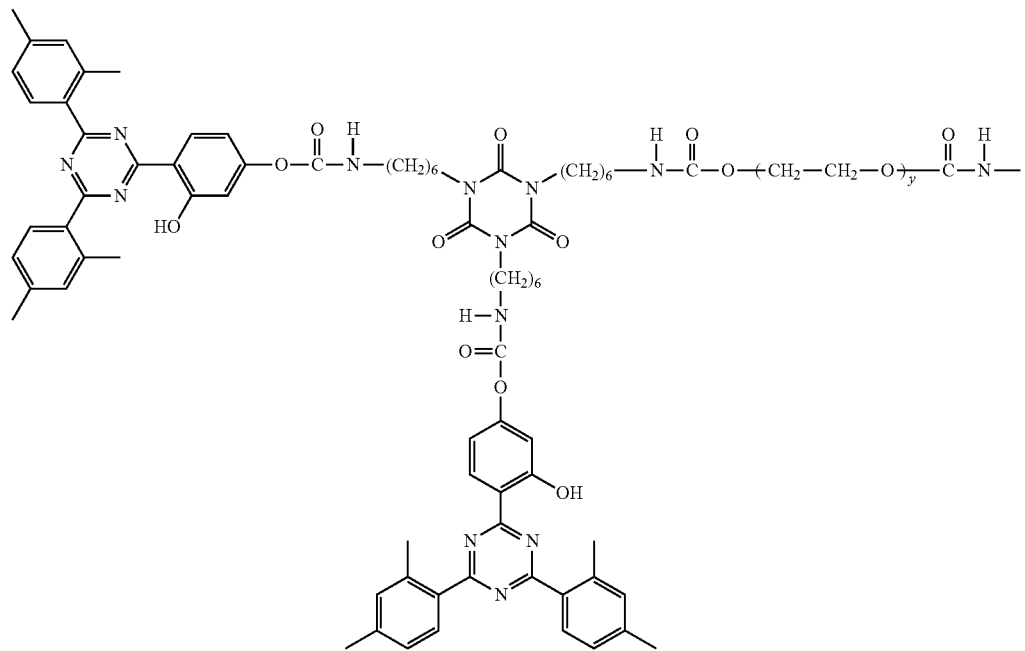

Figure 6:
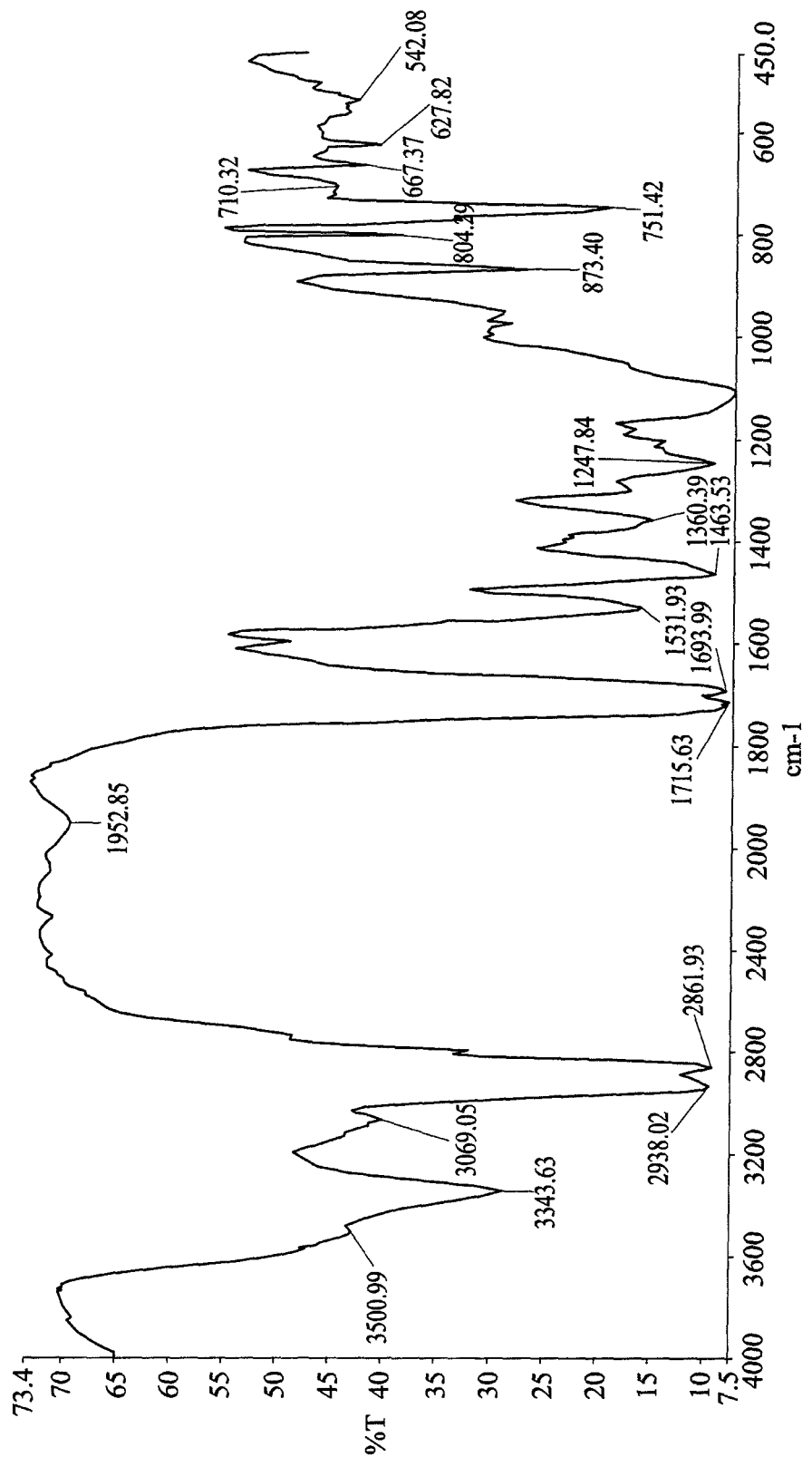
FIG. 6 is the IR spectrum according to the fifth embodiment of the present invention.

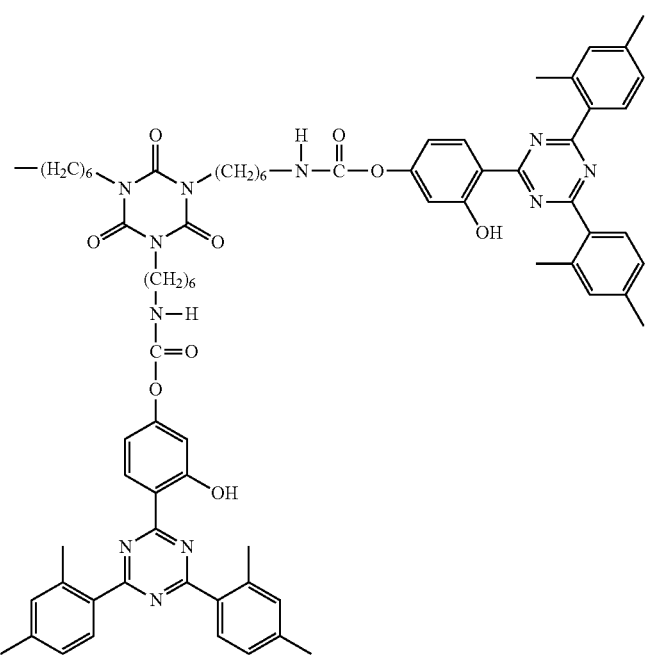

col, Mw=1000). The mixture was heated to 90° C., and the reaction was performed for 2-3 hours (the NCO group was titrated till the end point of the reaction). Then, the mixture was cooled down to 50° C., and then the compound 5 having the following structure was obtained (Mw=4489.2, IR spectrum shown in FIG. 6, —NH peak sharp 3343.63 cm-1, C=O peak sharp 1693.99~1715.63 cm-1). As shown in FIG. 6, the two peaks indicated the NHCOO group, which was the specific group of PU and resulted from the reaction of —NCO and —OH. Referring to FIG. 1 and FIG. 6, there was a significant —NCO peak at 2313.18 cm-1 in THDI plot, but there is no —NCO peak in FIG. 6 indicating that the reaction of —NCO and —OH was performed completely.

Embodiment 6: Compound 6

10.12 g of EV80 was provided in a 50 ml flask, stirred, heated to 50° C., and added with 4.04 g of THDI and 3.55 g of DMAc. The mixture was heated to 90° C., and the reaction was performed for 2-3 hours (the NCO group was titrated till the end point of the reaction). Then, the mixture was cooled down to 70° C., and then added with 1.22 g of DMAc and 0.53 g of DMBA (2,2-bis(hydroxymethyl)butyric acid). The mixture was heated to 90° C., and the reaction was performed for 2-3 hours (the NCO group was titrated till the end point of the reaction). Then, the mixture was cooled down to 50° C., and then the compound 6 having the following structure was obtained (Mw=3637.2, IR spectrum shown in FIG. 7, —NH

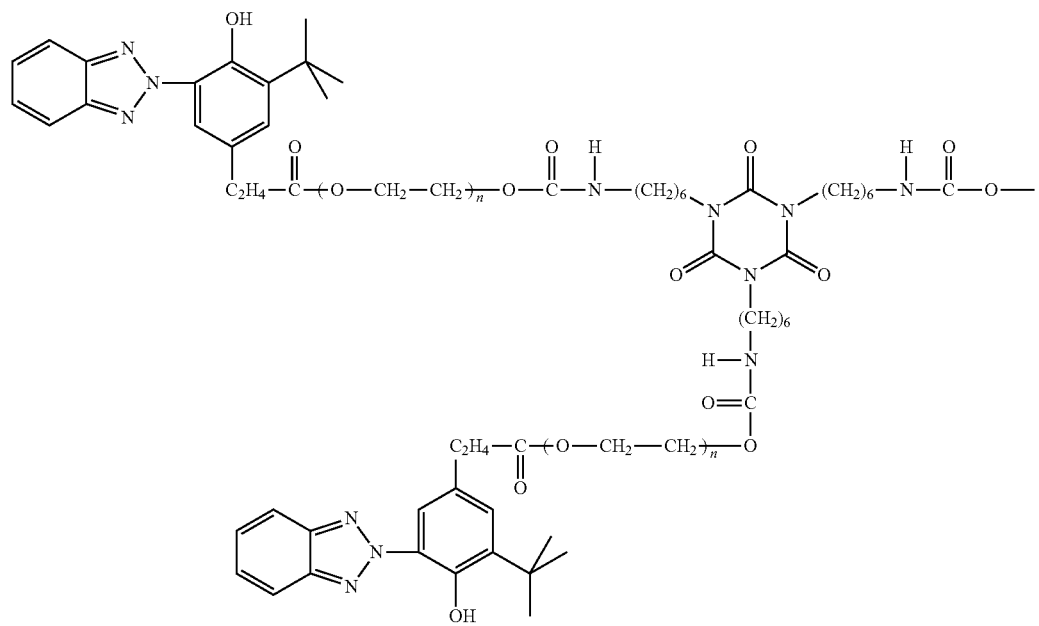

Figure 7:
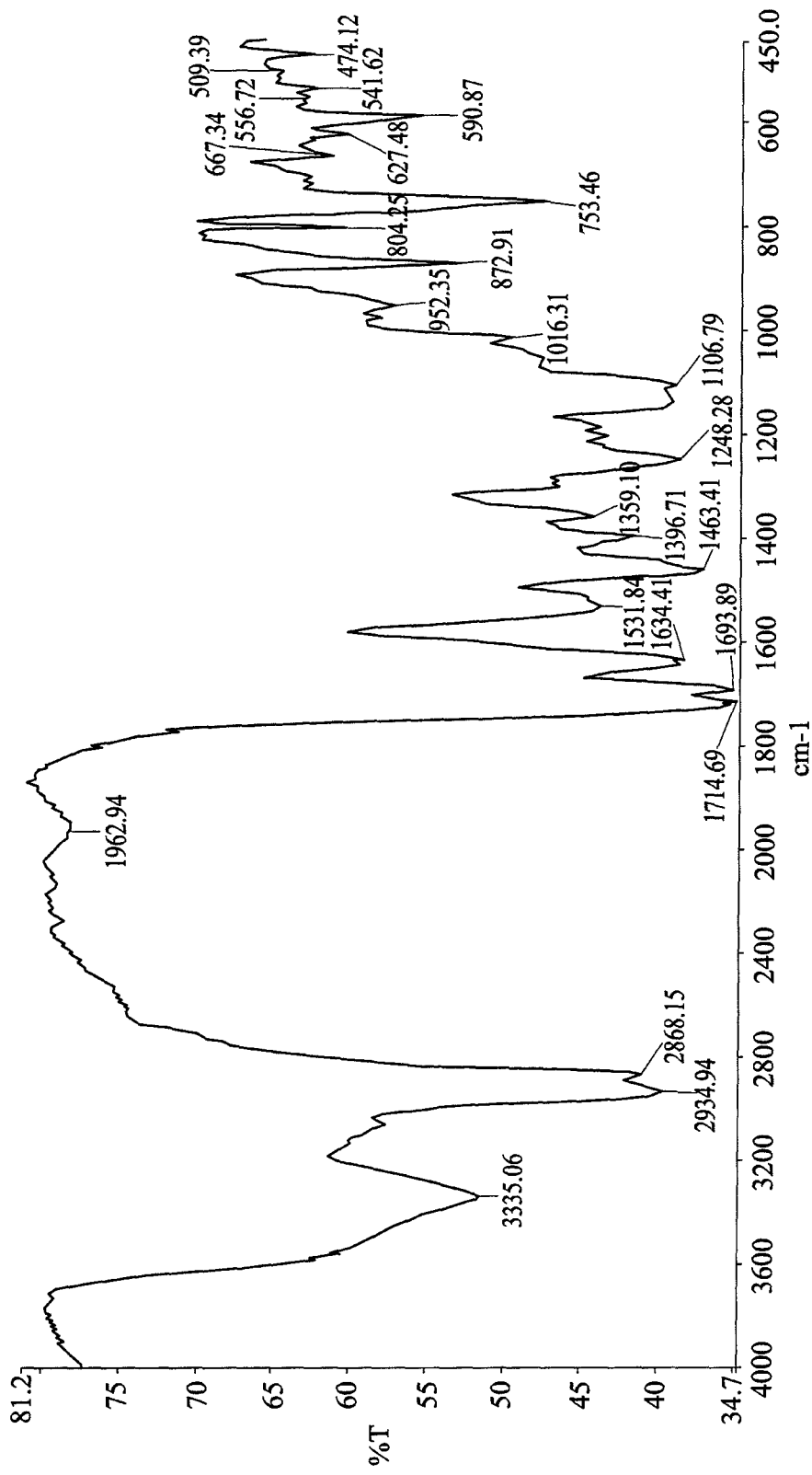
FIG. 7 is the IR spectrum according to the sixth embodiment of the present invention.

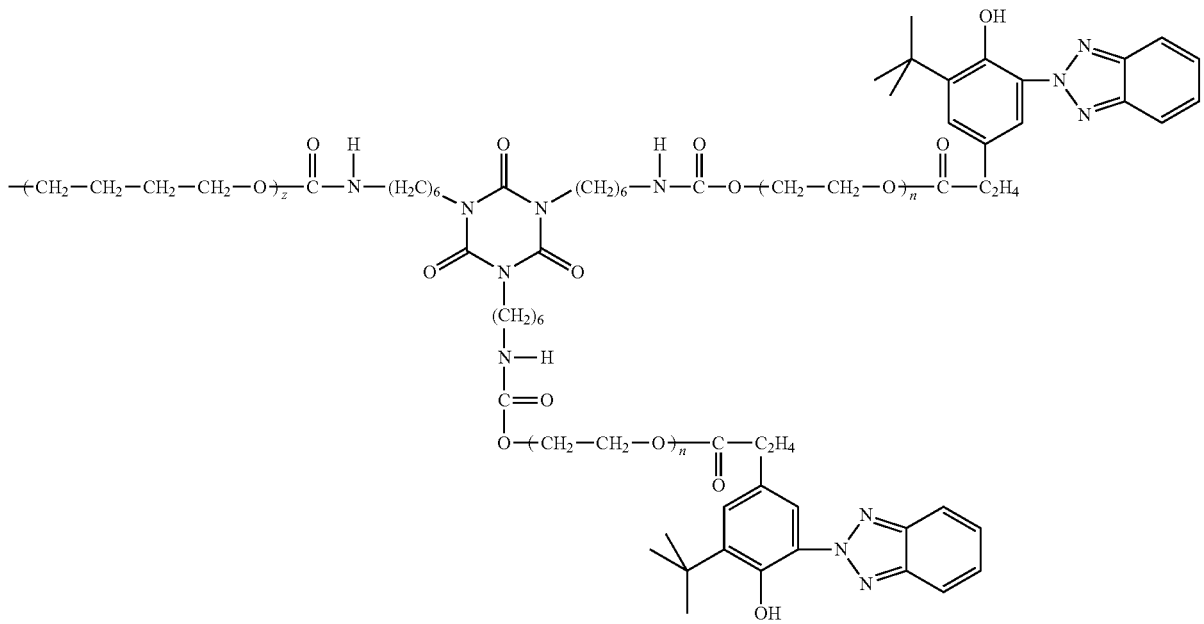

peak sharp 3335.06 cm-1, C=O peak sharp 1693.89~1714.69 cm-1). As shown in FIG. 7, the two peaks indicated the NHCOO group, which was the specific group of PU and resulted from the reaction of —NCO and —OH. Referring to FIG. 1 and FIG. 7, there was a significant —NCO peak at 2313.18 cm-1 in THDI plot, but there is no —NCO peak in FIG. 7 indicating that the reaction of —NCO and —OH was performed completely.

reaction). Then, the mixture was cooled down to 50° C., then added with 5.38 g of acetone and added with 1.68 g of EES-200L (sodium 2-(2-aminoethylamino)ethanesulfonate) (Taiwan Hopax Chems Mfg. Co., Ltd) drop by drop. The mixture was stirred for 30 minutes (the NCO group was titrated till the end point of the reaction), and then the compound 7 was obtained (Mw=3679.2, IR spectrum shown in FIG. 8, —NH peak sharp 3346.90 cm-1, C=O peak sharp

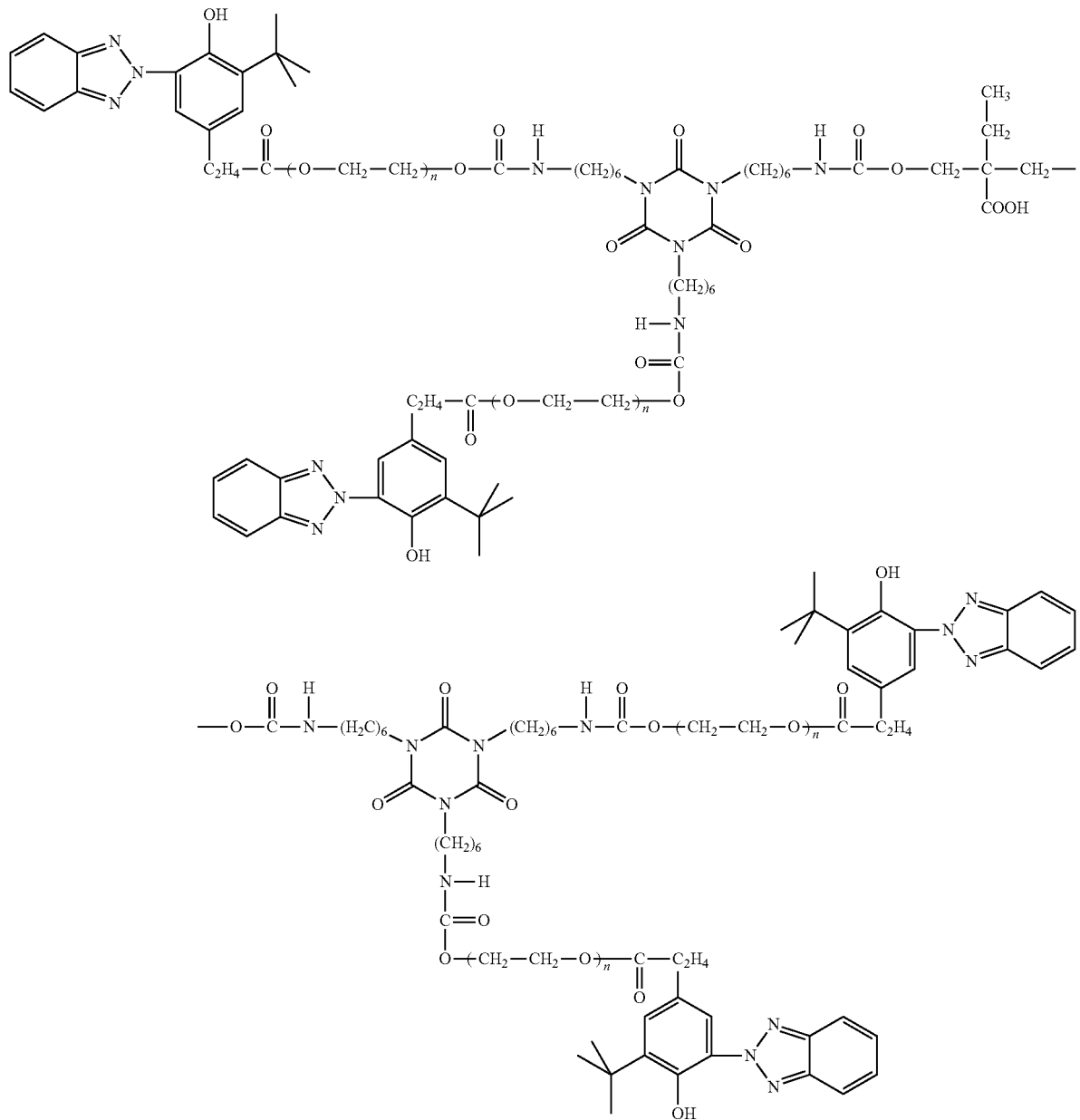

While using the compound 6, the compound 6 is added with 0.35 g of DMEA (N,N-dimethylethanolamine), stirred for 30 minutes for neutralization, then added with 26.2 g pure water and stirred at a high speed till dispersed completely.

Embodiment 7: Compound 7

Figure 8:
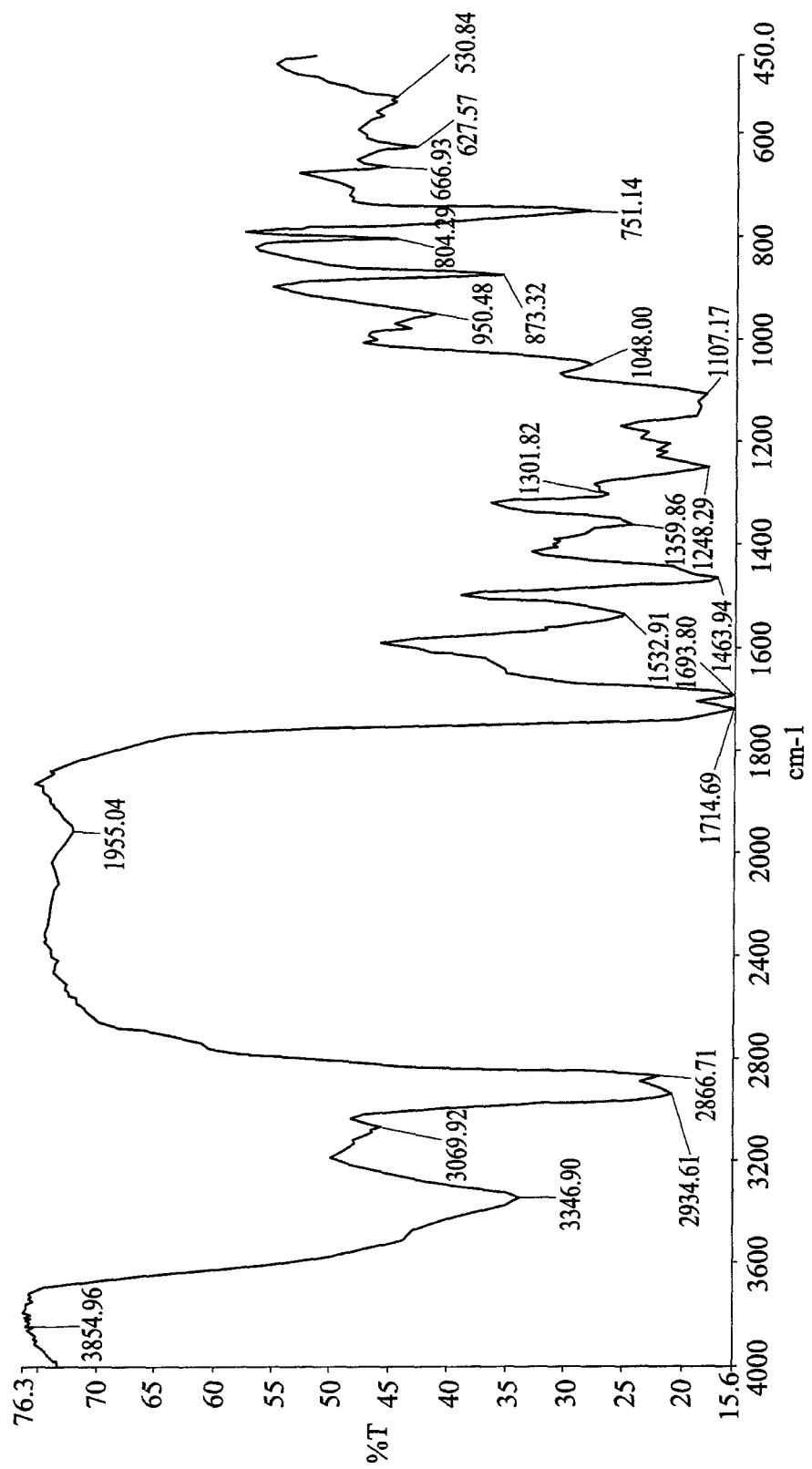
FIG. 8 is the IR spectrum according to the seventh embodiment of the present invention.

10.88 g of EV80 was provided in a 50 ml flask, stirred, heated to 50° C., and added with 4.34 g of THDI. The mixture was heated to 90° C., and the reaction was performed for 2-3 hours (the NCO group was titrated till the end point of the 1693.80~1714.69 cm-1). As shown in FIG. 8, the two peaks indicated the NHCONH group and the NHCON ($C_2H_4SO_3Na$), which were the specific groups of PU and resulted from the reactions of —NCO, —$NH_2$ and —NH ($C_2H_4SO_3Na$). Referring to FIG. 1 and FIG. 8, there was a significant —NCO peak at 2313.18 cm-1 in THDI plot, but there is no —NCO peak in FIG. 8 indicating that the reaction of —NCO, —$NH_2$ and —NH($C_2H_4SO_3Na$) was performed completely.

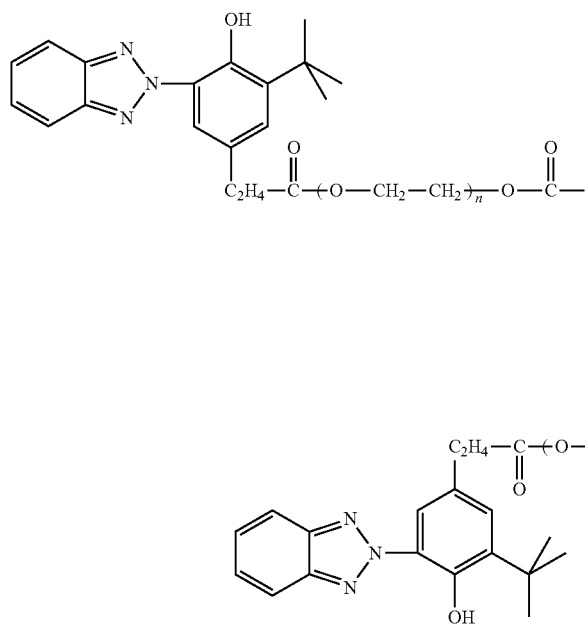
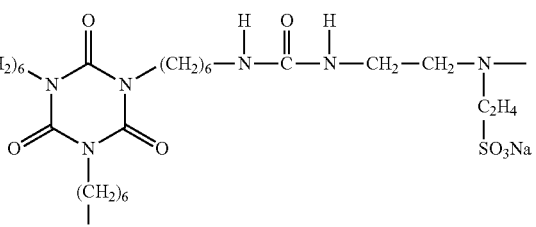
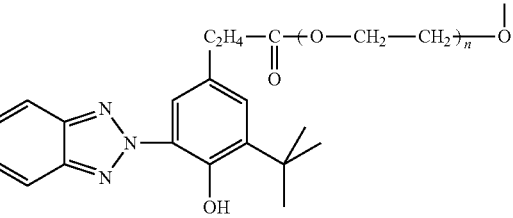
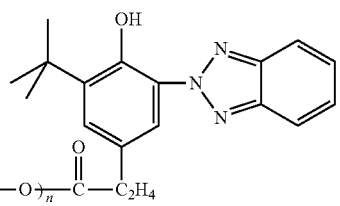
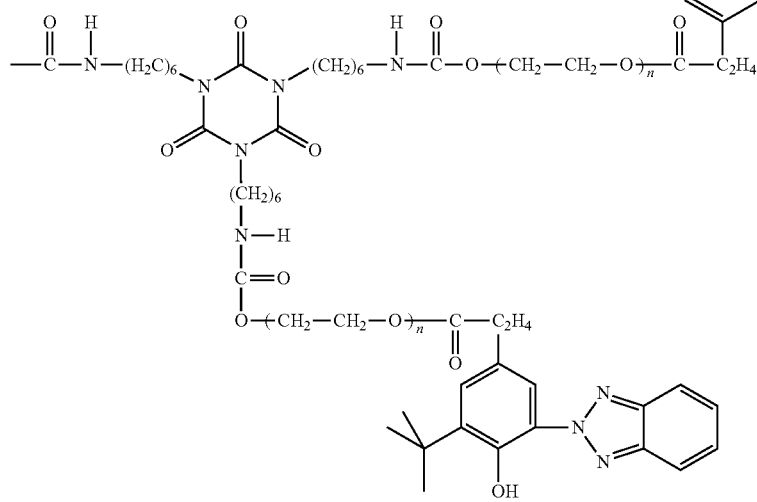

While using the compound 7, the compound 7 can be added with 28.1 g of pure water, and stirred at a high speed till dispersed completely.

Embodiment 8: Compound 8

Figure 9:
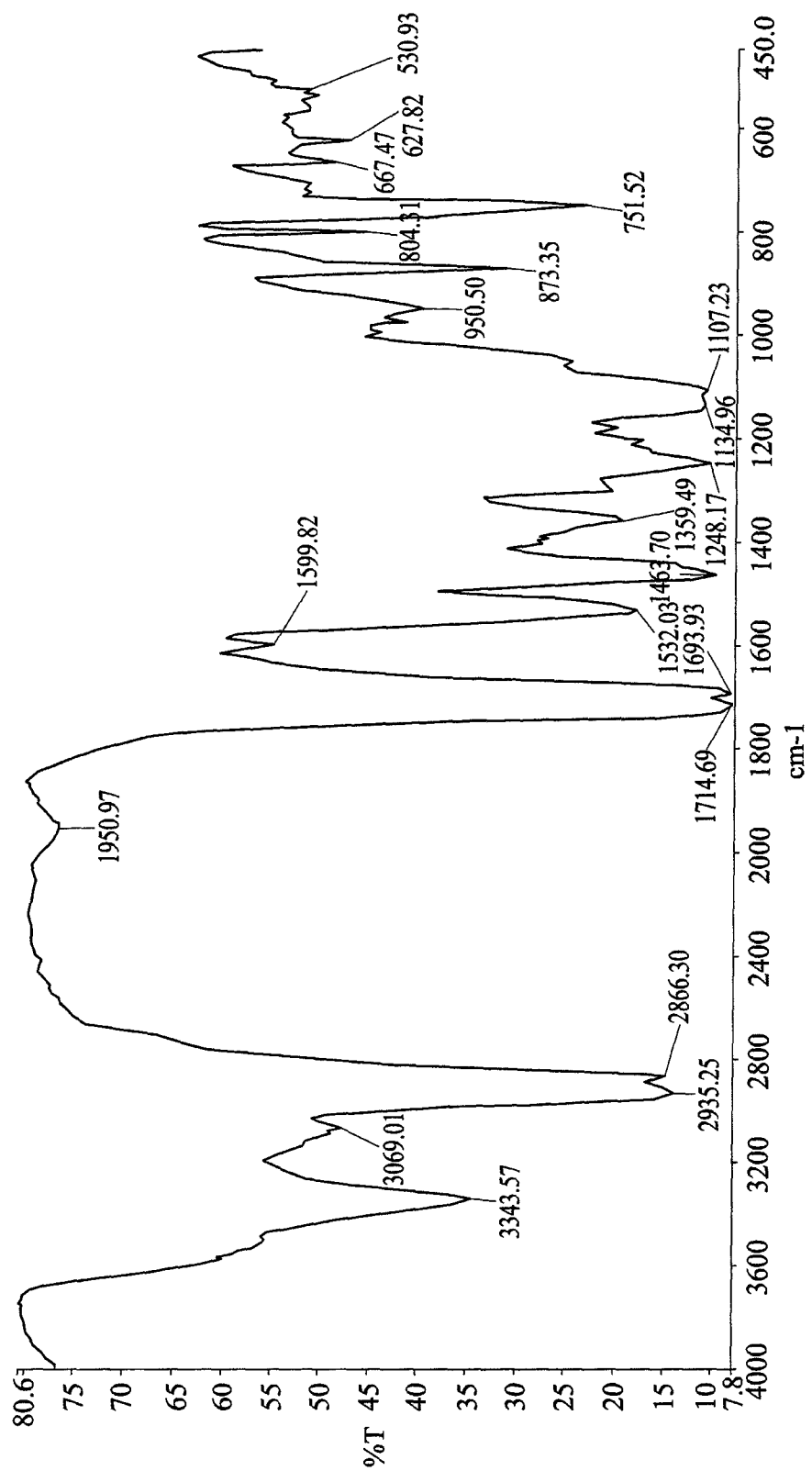
FIG. 9 is the IR spectrum according to the eighth embodiment of the present invention.

55.67 g of EV80 was provided in a 250 ml flask, stirred, heated to 50° C., and added with 22.20 g of THDI and 19.50 g of DMAc. The mixture was heated to 90° C., and the reaction was performed for 2-3 hours (the NCO group was titrated till the end point of the reaction). Then, the mixture was cooled down to 70° C., and then added with 2.59 g of MDEA (N-methyldiethanolamine) neutralized by 1.30 g of AcOH (Acetic Acid) and 7.20 g of DMAc. The mixture was heated to 90° C., and the reaction was performed for 2-3 hours (the NCO group was titrated till the end point of the reaction). Then, the mixture was cooled down to 50° C., and then the compound 8 having the following structure was obtained (Mw=3608.4, IR spectrum shown in FIG. 9, —NH peak sharp 3343.57 cm-1, C=O peak sharp 1693.93~1714.69 cm-1). As shown in FIG. 9, the two peaks indicated the NHCOO group, which was the specific group of PU and resulted from the reaction of —NCO and —OH. Referring to FIG. 1 and FIG. 9, there was a significant —NCO peak at 2313.18 cm-1 in THDI plot, but there is no —NCO peak in FIG. 9 indicating that the reaction of —NCO and —OH was performed completely.

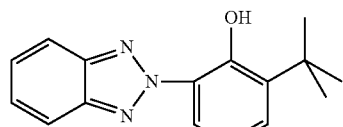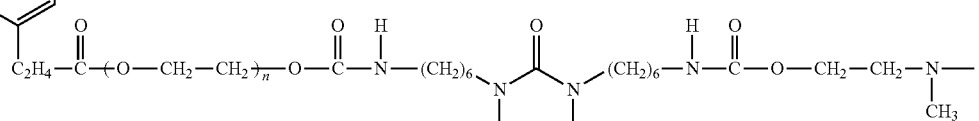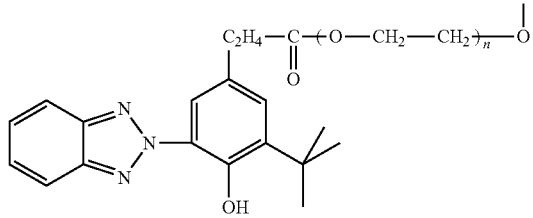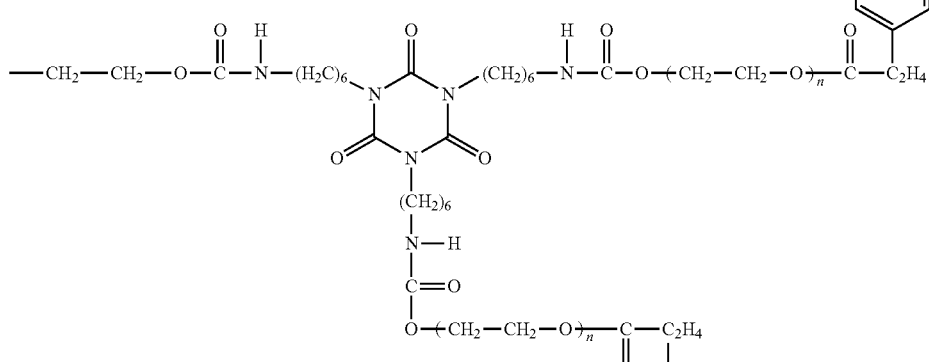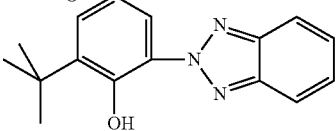

While using the compound 8, the compound 8 can be added with 158 g of pure water, and stirred at a high speed till dispersed completely.

Embodiment 9: Compound 9

Preparation of MPEDEA (Copolymer of Hexamethylene Diisocyanate, Methoxy Polyethylene Glycol and Triethanolamine)

35.52 g of MPEG 750 (methoxy poly(ethylene glycol), Mw=750) was provided in a 250 ml flask, stirred, heated to 50° C., and then added with 7.90 g of HDI (hexamethylene diisocyanate). The mixture was heated to 90° C., and the reaction was performed for 2-3 hours (the NCO group was titrated till the end point of the reaction). Then, the mixture was cooled down to 70° C., and then added with 6.74 g of TEA (2,2',2"-nitrilotriethanol). The mixture was heated to 90° C., and the reaction was performed for 2-3 hours (the NCO group was titrated till the end point of the reaction). Then, MPEDEA (Mw=1067.2) was obtained.

Figure 10:
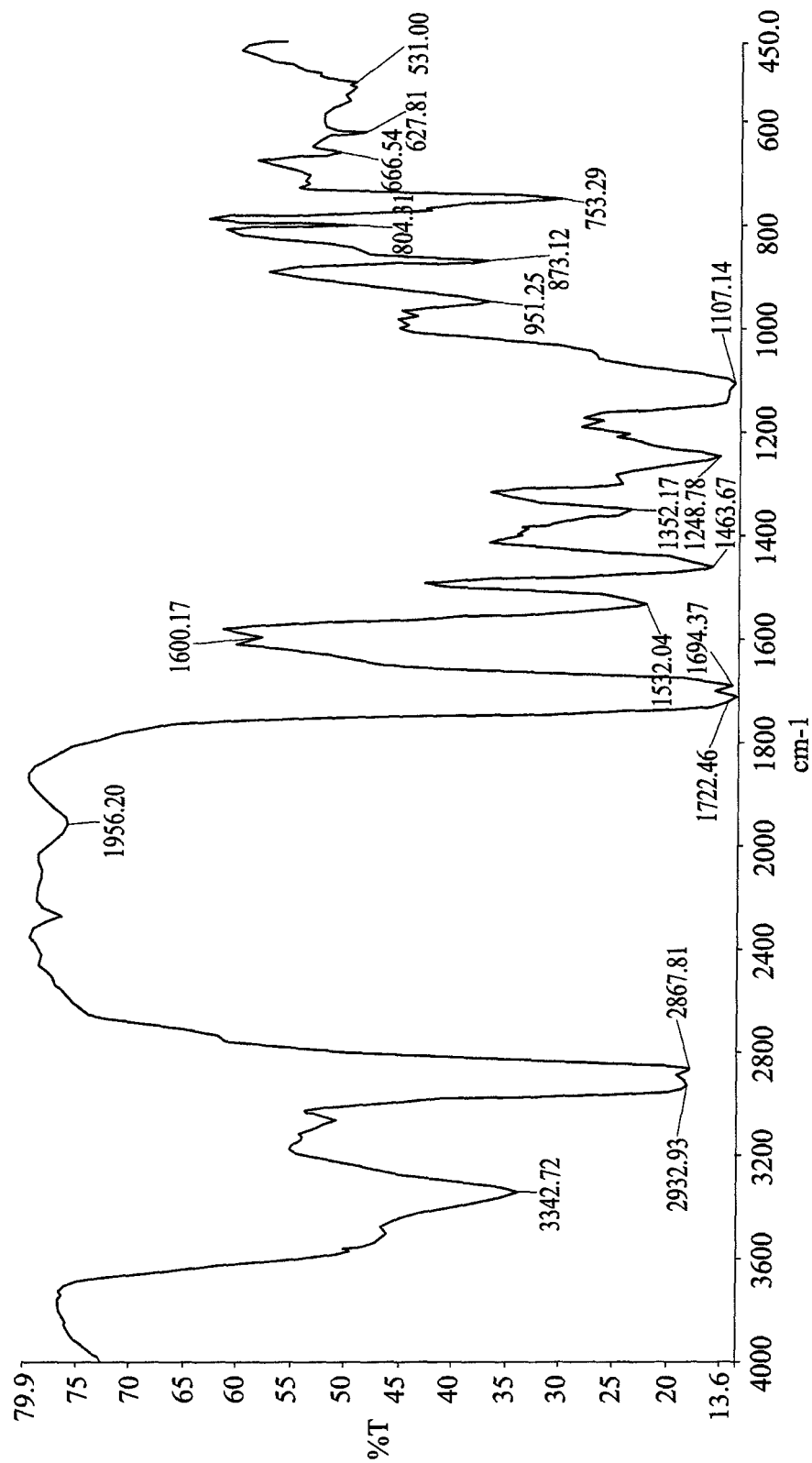
FIG. 10 is the IR spectrum according to the ninth embodiment of the present invention.

Then, 9.11 g of EV80 was provided in a 50 ml flask, stirred, heated to 50° C., and added with 3.63 g of THDI and 3.18 g of DMAc. The mixture was heated to 90° C., and the reaction was performed for 2-3 hours (the NCO group was titrated till the end point of the reaction). Then, the mixture was cooled down to 70° C., and added with 3.42 g of MPEDEA and 2.08 g of DMAc. The mixture was heated to 90° C., and the reaction was performed for 2-3 hours (the NCO group was titrated till the end point of the reaction). Then, the mixture was cooled down to 50° C., and then the compound 9 was obtained (Mw=4556.4, IR spectrum shown in FIG. 10, —NH peak sharp 3342.72 cm-1, C═O peak sharp 1694.37~1722.46 cm-1). As shown in FIG. 10, the two peaks indicated the NHCOO group, which was the specific group of PU and resulted from the reaction of —NCO and —OH. Referring to FIG. 1 and FIG. 10, there was a significant —NCO peak at 2313.18 cm-1 in THDI plot, but there is no —NCO peak in FIG. 10 indicating that the reaction of —NCO and —OH was performed completely.

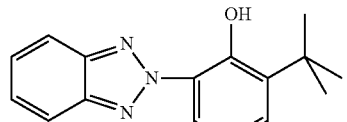

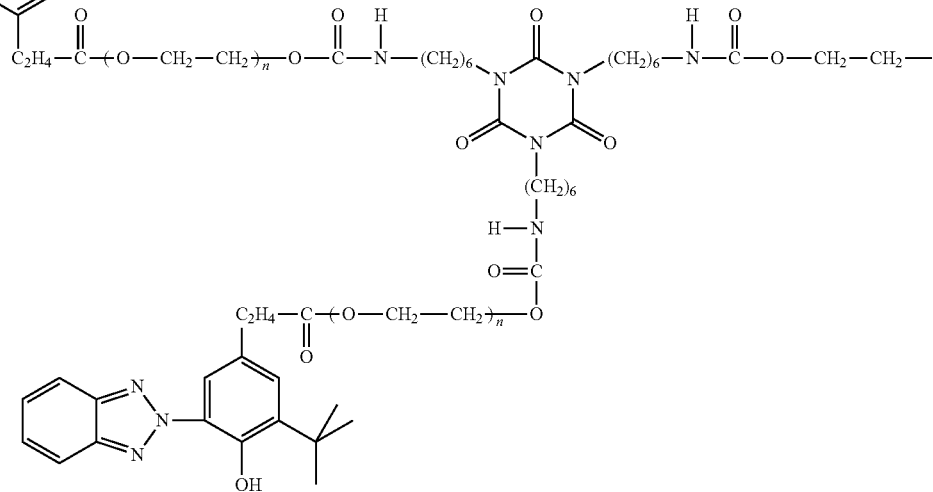

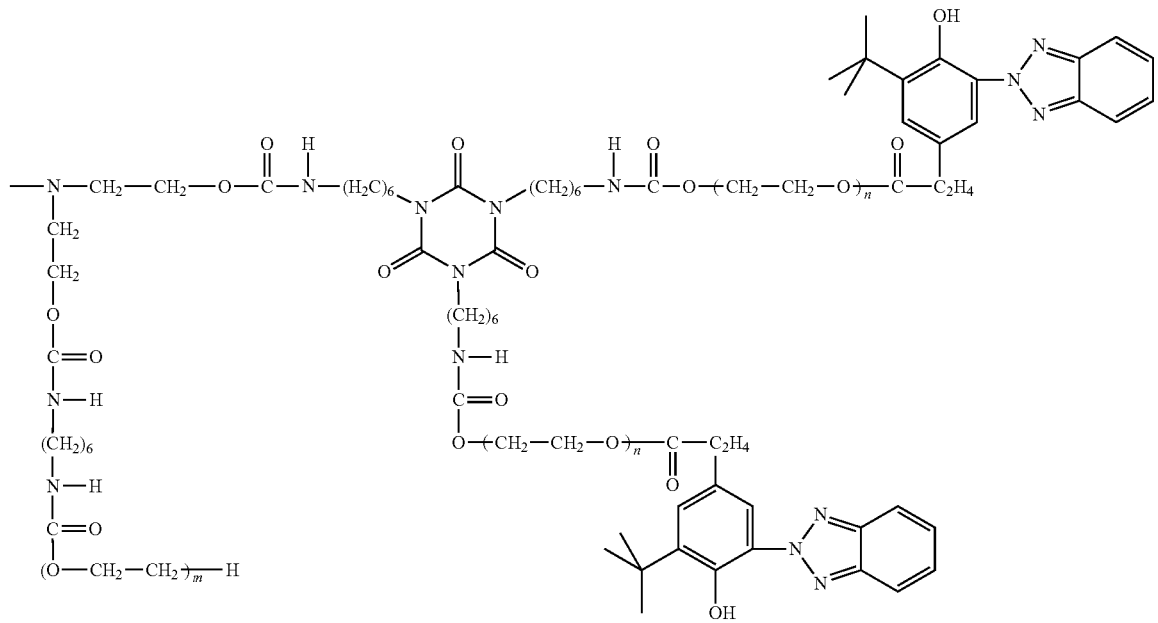

While using the compound 9, the compound 9 was added with 0.19 g of AcOH, stirred for neutralization for 30 minutes, then added with 29.3 g of pure water and stirred at a high speed till dispersed completely.

Embodiment 10: Compound 10

Figure 11:
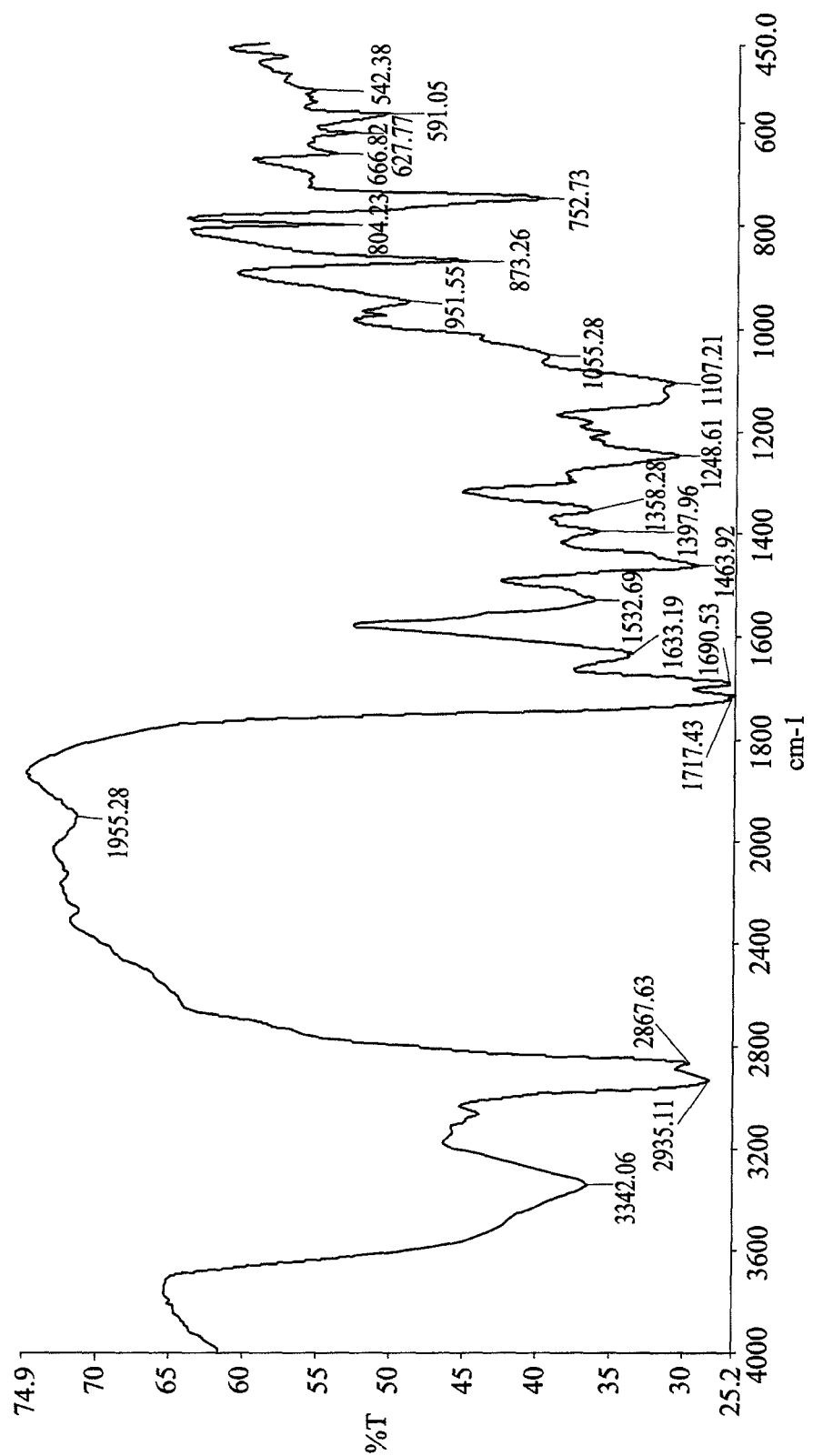
FIG. 11 is the IR spectrum according to the tenth embodiment of the present invention.

19.58 g of EV80 was provided in a 100 ml flask, stirred, heated to 50° C., and added with 7.57 g of THDI and 6.77 g of DMAc. The mixture was heated to 90° C., and the reaction was performed for 2-3 hours (the NCO group was titrated till the end point of the reaction). Then, the mixture was cooled down to 70° C., and added with 2.30 g of DMAc and 0.89 g of DMPA (2,2-bis(hydroxymethyl)propionic acid). The mixture was heated to 90° C., and the reaction was performed for 2-3 hours (the NCO group was titrated till the end point of the reaction). Then, the mixture was cooled down to 50° C., and then the compound 10 was obtained (Mw=3623.2, IR spectrum shown in FIG. 11, —NH peak sharp 3342.06 cm-1, C=O peak sharp 1690.53~4717.43 cm-1). As shown in FIG. 11, the two peaks indicated the NHCOO group, which was the specific group of PU and resulted from the reaction of —NCO and —OH. Referring to FIG. 1 and FIG. 11, there was a significant —NCO peak at 2313.18 cm-1 in THDI plot, but there is no —NCO peak in FIG. 11 indicating that the reaction of —NCO and —OH was performed completely.

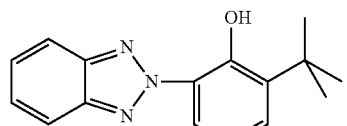
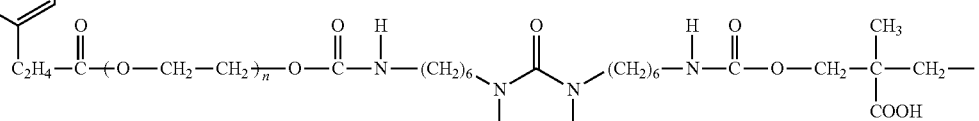
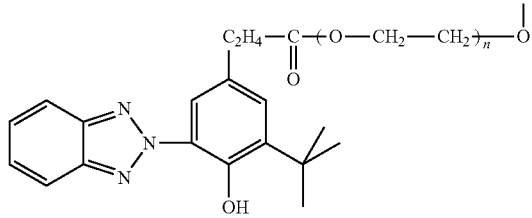
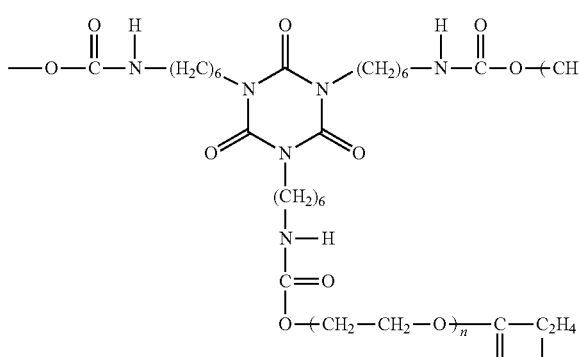
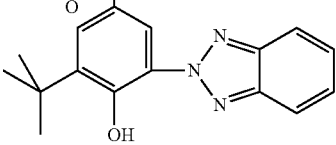

While using the compound 10, the compound 10 was added with 0.59 g of DMEA, stirred for neutralization for 30 minutes, then added with 50 g of pure water and stirred at a high speed till dispersed completely.

Preparation of Compositions 1-2

Embodiment 11: Composition 1

Figure 12:
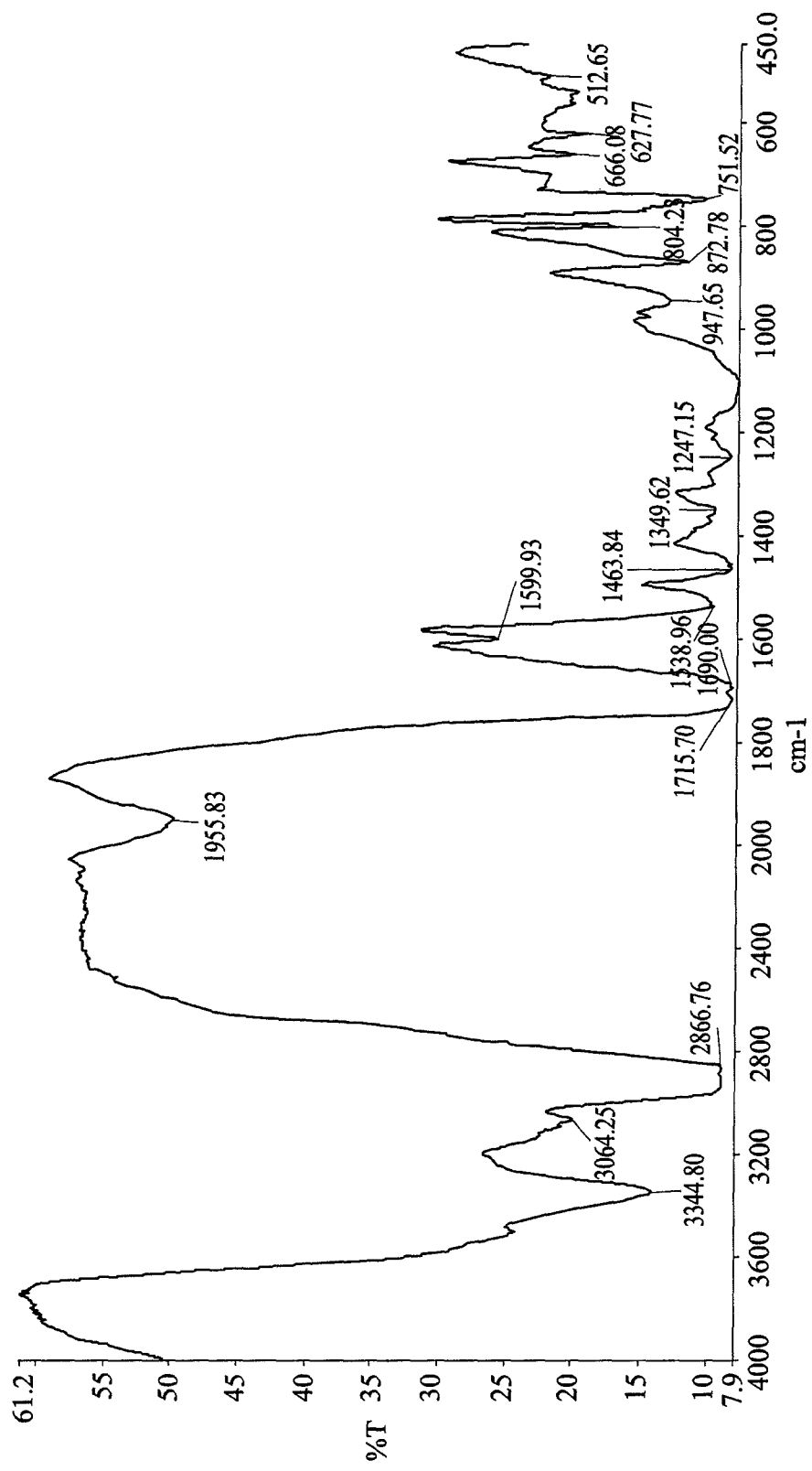
FIG. 12 is the IR spectrum according to the eleventh embodiment of the present invention.

46.82 g of EV80 was provided in a 250 ml flask, stirred, heated to 50° C., and added with 18.67 g of THDI and 16.40 g of DMAc. The mixture was heated to 90° C., and the reaction was performed for 2-3 hours (the NCO group was titrated till the end point of the reaction). Then, the mixture was cooled down to 70° C., and added with 11.30 g of DMAc, 1.63 g of PPG 1000 and 16.35 g of PEG 1000 (PPG 1000/PEG 1000=1/10 (mole/mole)). The mixture was heated to 90° C., and the reaction was performed for 2-3 hours (the NCO group was titrated till the end point of the reaction). Then, the mixture was cooled down to 50° C., and the composition 1 was obtained (IR spectrum shown in FIG. 12, —NH peak sharp 3344.80 cm-1, C=O peak sharp 1690.00~1715.70 cm-1). As shown in FIG. 12, the two peaks indicated the NHCOO group, which was the specific group of PU and resulted from the reaction of —NCO and —OH. Referring to FIG. 1 and FIG. 12, there was a significant —NCO peak at 2313.18 cm-1 in THDI plot, but there is no —NCO peak in FIG. 12 indicating that the reaction of —NCO and —OH was performed completely.

While using the composition 1, the composition 1 can be used with 163 g of pure water till dispersed completely.

Alternatively, the composition 1 may be mixed with the compound 1 (Embodiment 1) and the compound 2 (Embodiment 2), then the mixture was dispersed in water, and thus the solution of composition 1 was obtained.

Embodiment 12: Composition 2

Figure 13:
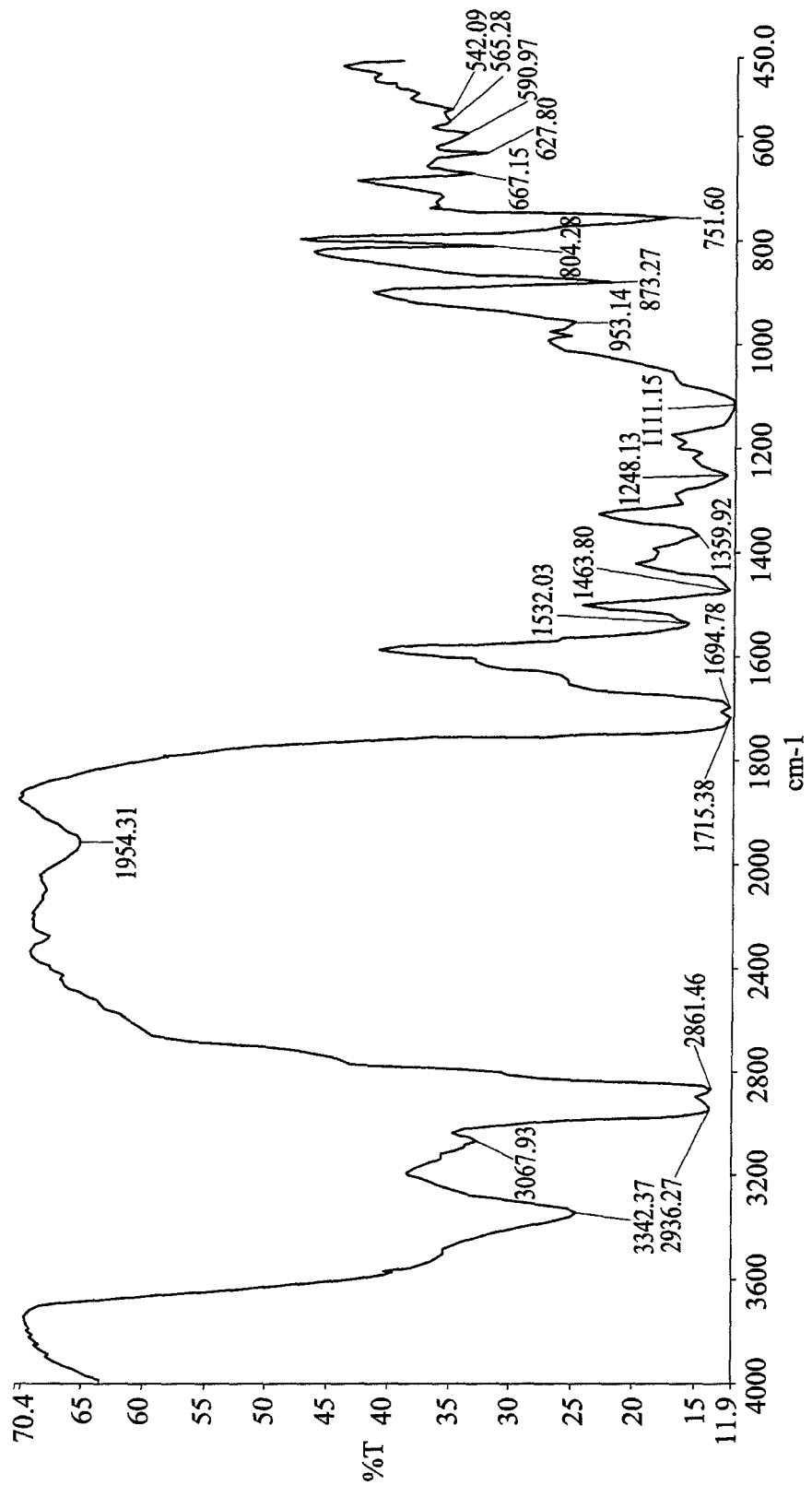
FIG. 13 is the IR spectrum according to the twelfth embodiment of the present invention.

41.76 g of EV80 was provided in a 250 ml flask, stirred, heated to 50° C., and added with 16.65 g of THDI and 14.60 g of DMAc. The mixture was heated to 90° C., and the reaction was performed for 2-3 hours (the NCO group was titrated till the end point of the reaction). Then, the mixture was cooled down to 70° C., and added with 7.80 g of DMAc, 8.09 g of PTMG 1000 and 1.08 g of DMPA (PTMG 1000/ DMPA=1/1 (mole/mole)). The mixture was heated to 90° C., and the reaction was performed for 2-3 hours (the NCO group was titrated till the end point of the reaction). Then, the mixture was cooled down to 50° C., and the composition 2 was obtained (IR spectrum shown in FIG. 13, —NH peak sharp 3342.37 cm-1, C=O peak sharp 1694.78~1715.38 cm-1). As shown in FIG. 13, the two peaks indicated the NHCOO group, which was the specific group of PU and resulted from the reaction of —NCO and —OH. Referring to FIG. 1 and FIG. 13, there was a significant —NCO peak at 2313.18 cm-1 in THDI plot, but there is no —NCO peak in FIG. 13 indicating that the reaction of —NCO and —OH was performed completely.

While using the composition 2, the composition 2 can be added with 0.72 g of DMEA, stirred for 30 minutes for neutralization, then added with 177 g of pure water, and stirred at a high speed till dispersed completely.

Alternatively, the composition 2 may be mixed with the compound 5 (Embodiment 5) and the compound 10 (Embodiment 10), then the mixture was dispersed in water, and thus the solution of composition 2 was obtained.

to 80° C., and added with a pre-mixture of 5.01 g of HDI, 7.8 g of MEK and 0.09 g of DBTL (dibutyltin dilaurate). The reaction was performed at 80° C. for 45 minutes. After titration, the mixture was added with 2.5 g of HDI and 13.97 g of BTZ-diol

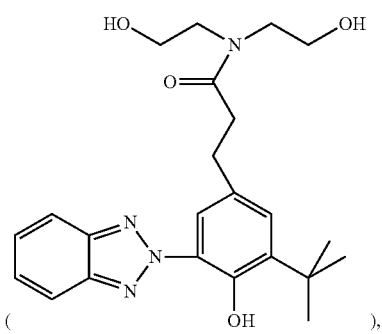 [SMILES: CC(C)(C)c1cc(CCC(=O)N(CCO)CCO)cc(-n2nc3ccccc3n2)c1O]

then the reaction was performed for 1 hour, and thus the compound having the following structure was obtained.

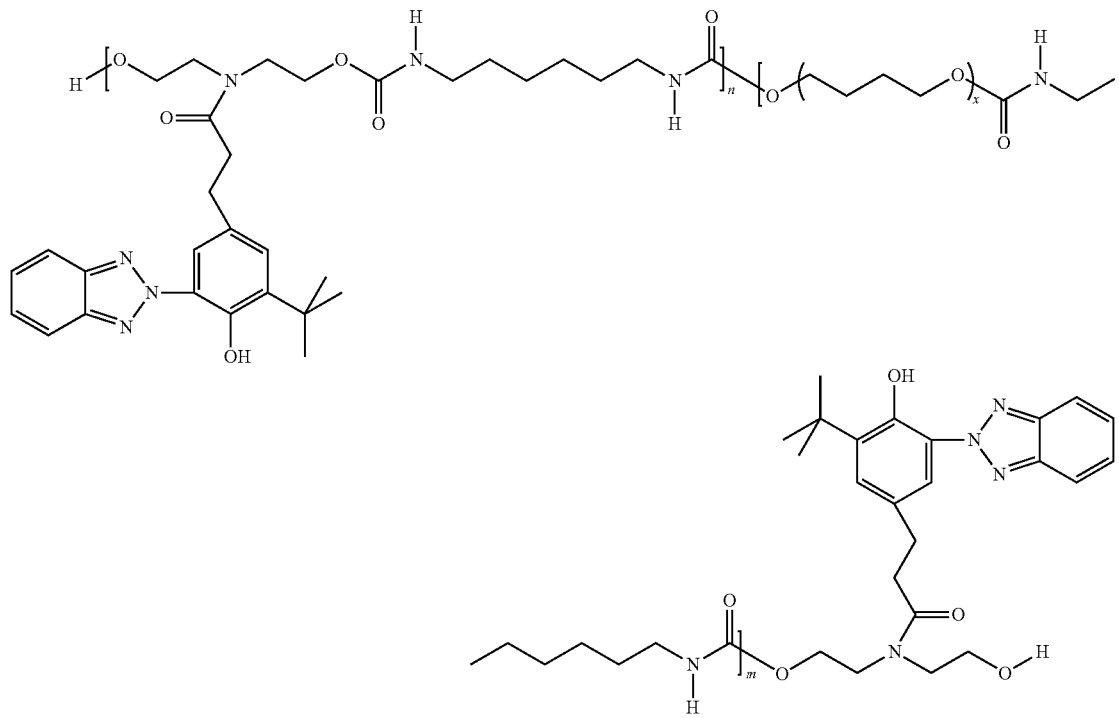

In accordance with the present invention, while using the compound or the composition of the present invention, the compound or the composition of the present invention can be added with water without any surfactant to form a solution for treating a substrate (for example, a textile). Certainly, in order to achieve a specific purpose, the compound or the composition of the present invention may be optionally added with an additive (for example, a surfactant).

COMPARATIVE EXAMPLE 1

29.93 g of PTMG 2000 (Mw=2000) and 44.1 g of MEK were provided in a 250 ml flask, stirred under nitrogen, heated

COMPARATIVE EXAMPLE 2

10 g of BTZ-diol and 2 g of toluene were provided in a 50 ml flask, stirred under nitrogen, and heated to 110° C. After the mixture was clean, the mixture was cooled down to 72° C., and then added with 12 g of MEK and a pre-mixture of 3.46 g of HDI, 5.2 g of MEK and 0.027 g of DBTL. The reaction was performed at 72° C. for 45 minutes. After titration, the mixture was added with a mixed solution of 0.69 g of MDEA and 1.03 g of MEK, and then the reaction was performed at 60° C. for 15 minutes. Then, the compound having the following structure was obtained.

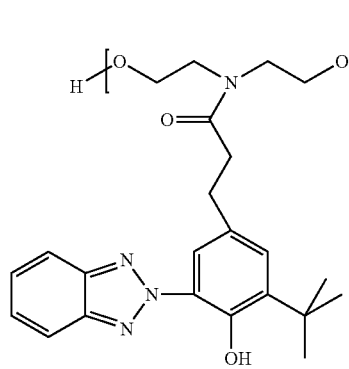
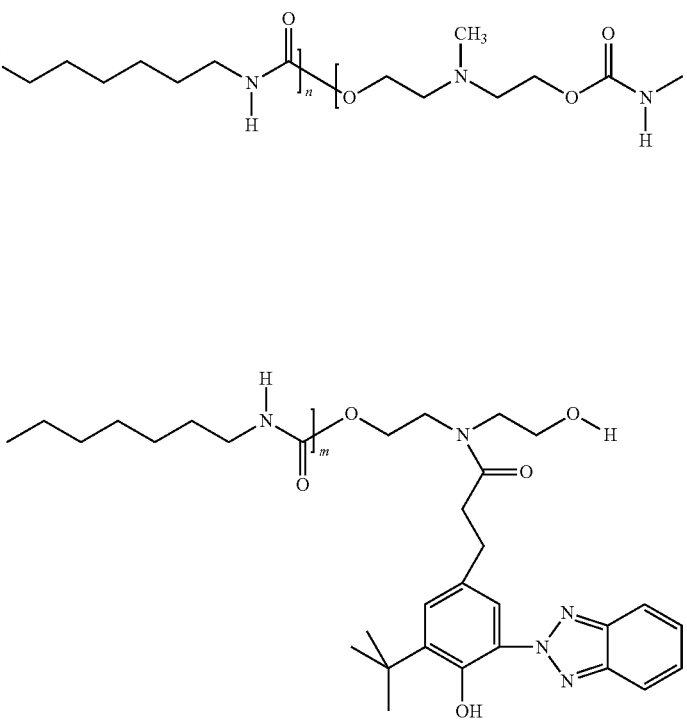

While using the compounds of Comparative Examples 1 and 2, the compounds need to be added with surfactants for emulsification to form an aqueous emulsion.

The compound of formula (I) and the composition of the present invention can be formed as a solution without a surfactant. Further, in accordance with the present invention, there is only extremely low amount of the organic solvent in the composition. In the prior art, the UV absorbing agent (such as the compounds of Comparative Examples 1 and 2) has a significant amount of organic solvents (about 60-95%), and needs to be added with surfactants to form an emulsion (for example, the compound of Comparative Example 1 needs the surfactant).

Test of Light Fastness

The dispersion solution (30 g/L (50 g/L for the compound 4 of Embodiment 4)) of the compound or the composition of above Embodiments and Comparative Examples was tested for light fastness. The results were shown in Tables 1-3. The larger grade number indicated better light fastness.

100 ml of the dispersion solution was poured into a roller of a pad dyeing machine and absorbed by a textile. Then, the textile was dried at 60° C., and the light fastness of the textile was analyzed by AATCC 16-3(20AFU). The textile without any dispersion solution was used as a blank.

TABLE 1

| Number | Grade |
|---|---|
| Blank | 3 |
| Comparative Example 1 | precipitated |
| Embodiment 11 | 3.5 |
| Embodiment 2 | 3.5 |
| Embodiment 3 | 3.5 |
| Embodiment 4 | 3.5 |

TABLE 2

| Number | Grade |
|---|---|
| Blank | 3 |
| Embodiment 12 | 4 |
| Embodiment 6 | 4 |
| Embodiment 7 | 4 |
| Embodiment 10 | 4 |

TABLE 3

| Number | Grade |
|---|---|
| Blank | 3 |
| Comparative Example 2 | 3.5 |
| Embodiment 8 | 4 |
| Embodiment 9 | 3.5 |

The polyurethane derivative of formula (I) and the composition of the present invention can be used for forming a solution without a surfactant. As shown in Tables 1 to 3, the polyurethane derivative of formula (I) and the composition of the present invention enhance the light fastness to the grade 3.5 to 4.

While using the compound of Comparative Example 1, there exists a significant amount of an organic solvent, and an additional surfactant needs to be added. In other words, if there is no surfactant added with the compound of Comparative Example 1, the light fastness cannot be measured. While using the compound of Comparative Example 2, there exists a significant amount of an organic solvent and poor light fastness improvement in comparison with the compound of Embodiment 8 of the present invention.

The polyurethane derivative of formula (I) and the composition of the present invention have great attachment and a great anti-UV characteristic to a substrate (for example, a textile), improve light fastness of a coating material (for example, a dye) applied on a substrate, and have great washing fastness.

Further, while using the polyurethane derivative of formula (I) and the composition of the present invention, there exists an extremely low amount of an organic solvent. Moreover, the polyurethane derivative of formula (I) and the composition of the present invention can be used for forming a solution without being added with a surfactant. Therefore, the polyurethane derivative of formula (I), the composition, and the additive (for example, a light fastness increasing agent) prepared from the polyurethane derivative of the present invention meet the trend of environmental protections.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. A polyurethane derivative having a structure of formula (I):

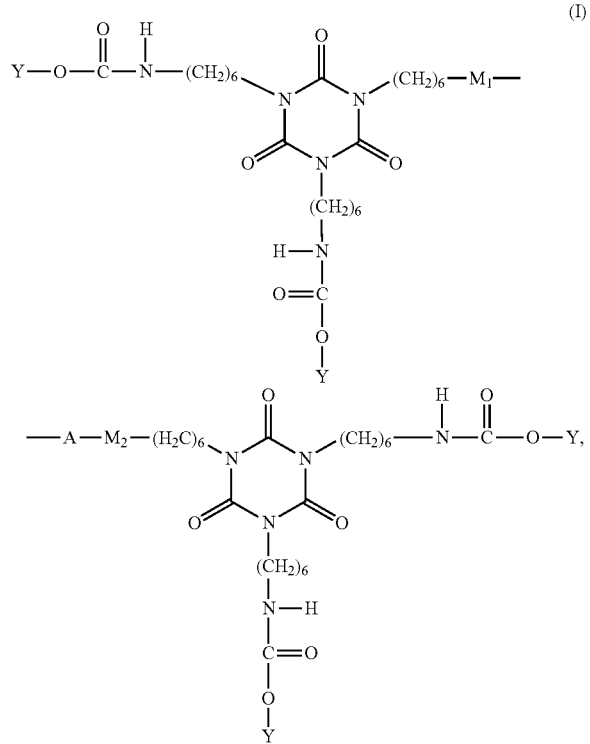

wherein A is one selected from the group consisting of

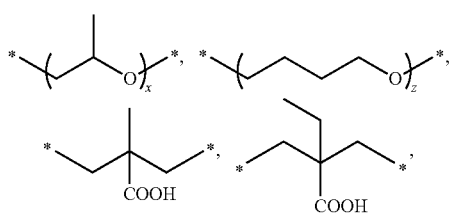

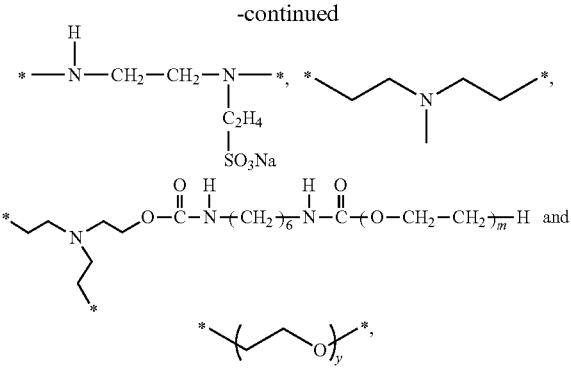

wherein x is an integer in a range of from 15 to 20, z is an integer in a range of from 10 to 15, m is an integer in a range of from 15 to 20, y is an integer in a range of from 20 to 50, and * indicates a position to be bound with M1 or M2, in which M1 and M2 are independently —NHCOO— or —NHCO—; and Y is one selected from the group consisting of

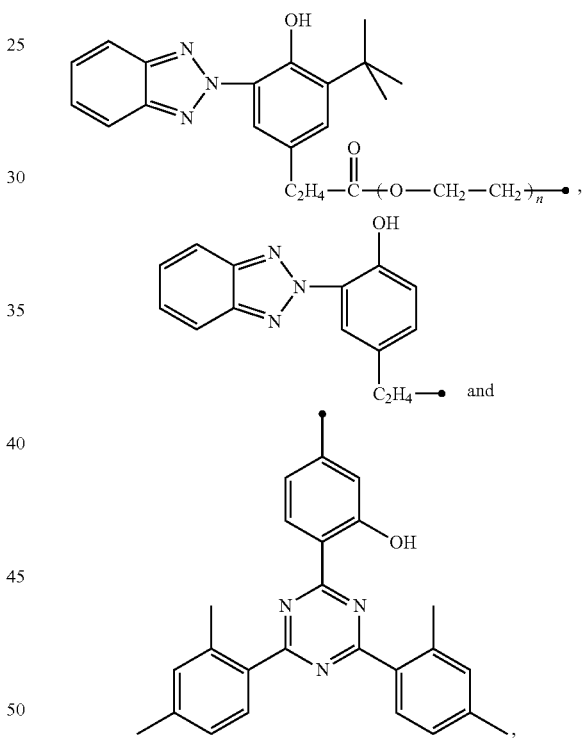

in which n is an integer in a range of from 7 to 9, ● indicates a position to be bound with —O—, and each Y is identical or different.

2. The polyurethane derivative of claim 1, wherein A is one selected from the group consisting of

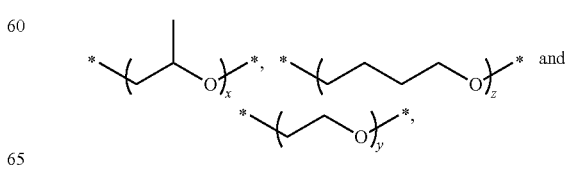

and M1 is different from M2.

3. The polyurethane derivative of claim 1, wherein A is one selected from the group consisting of

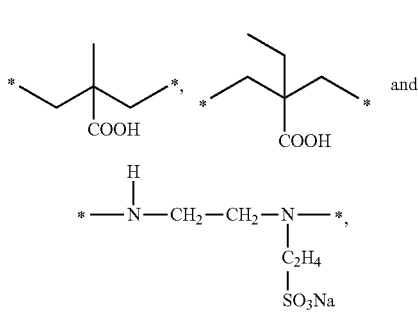

and M1 and M2 are the same.

4. The polyurethane derivative of claim 1, wherein A is

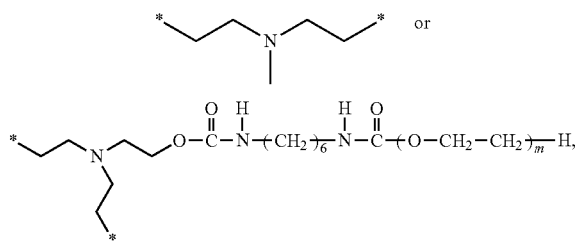

and M1 and M2 are the same.

5. The polyurethane derivative of claim 1, wherein Y is

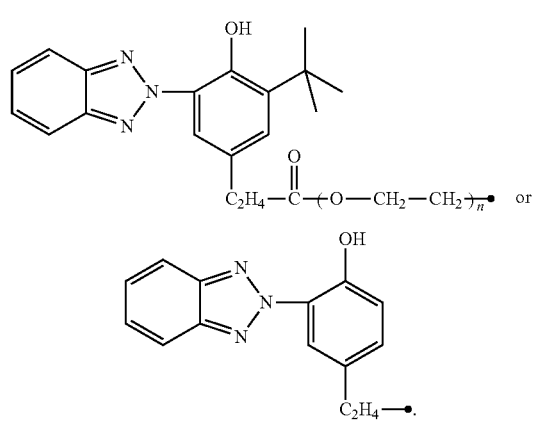

6. The polyurethane derivative of claim 5, wherein A is

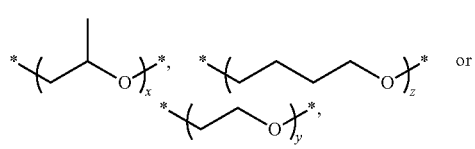

and M1 is different from M2.

7. The polyurethane derivative of claim 5, wherein A is

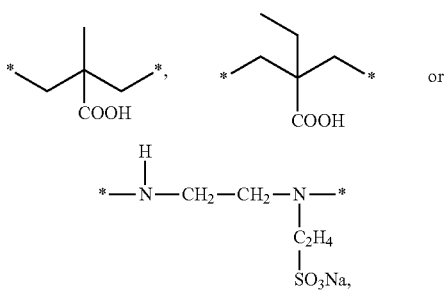

and M1 and M2 are the same.

8. The polyurethane derivative of claim 5, wherein A is

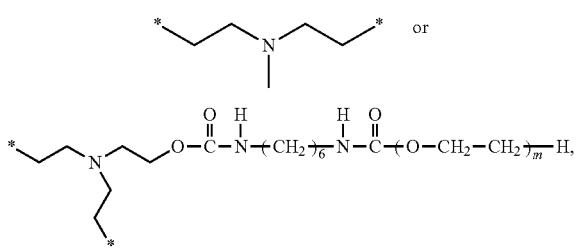

and M1 and M2 are the same.

9. The polyurethane derivative of claim 1, wherein Y is

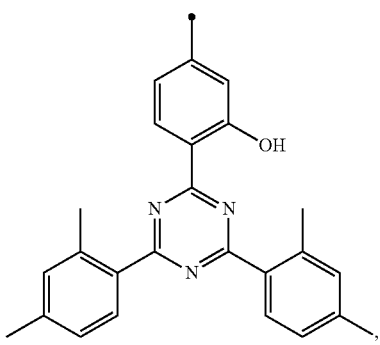

A is

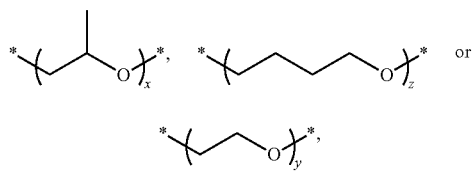

and M1 is different from M2.

10. A composition for increasing light fastness, comprising the polyurethane derivative of claim 1.

11. A composition of claim 10, comprising:
one polyurethane derivative of claim 1, wherein Y is

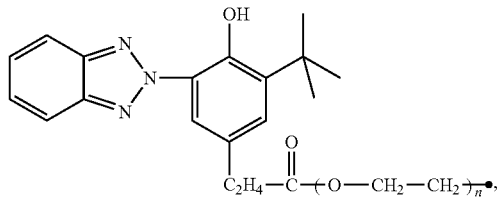

A is

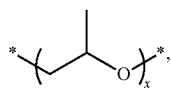

and M1 is different from M2; and
another polyurethane derivative of claim 1, wherein Y is

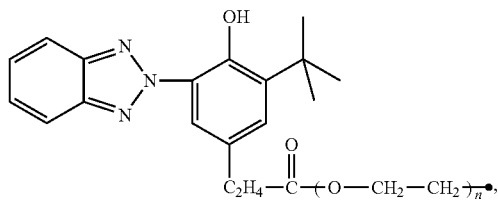

A is

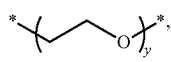

and M1 is different from M2.

12. A composition of claim 10, comprising:
one polyurethane derivative of claim 1, wherein Y is

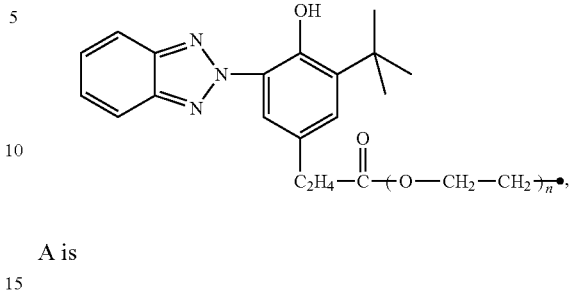

A is

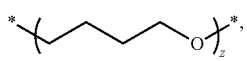

and M1 is different from M2; and
another polyurethane derivative of claim 1, wherein Y is

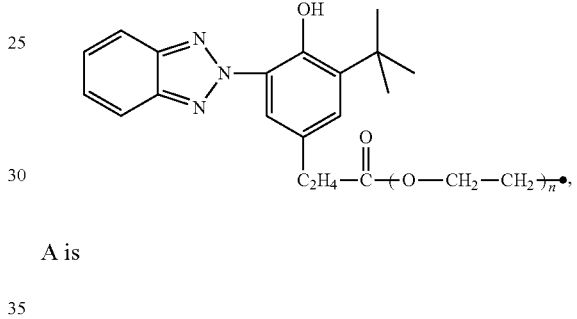

A is

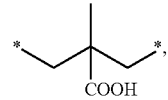

and M1 and M2 are independently —NHCOO—.

13. A dye additive, comprising the polyurethane derivative of claim 1.

* * * * *